US010398380B2

(12) United States Patent
Sano et al.

(10) Patent No.: US 10,398,380 B2
(45) Date of Patent: Sep. 3, 2019

(54) DROWSINESS DETECTION DEVICE, DROWSINESS DETECTION METHOD, AND COMPUTER-READABLE RECORDING MEDIUM STORING PROGRAM FOR DROWSINESS DETECTION

(71) Applicant: FUJITSU LIMITED, Kawasaki-shi, Kanagawa (JP)

(72) Inventors: Satoshi Sano, Kawasaki (JP); Yasuhiko Nakano, Kawasaki (JP); Yuichi Tanaka, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 287 days.

(21) Appl. No.: 15/263,809

(22) Filed: Sep. 13, 2016

(65) Prior Publication Data
US 2017/0079579 A1    Mar. 23, 2017

(30) Foreign Application Priority Data
Sep. 17, 2015  (JP) ................. 2015-184290

(51) Int. Cl.
*A61B 5/024* (2006.01)
*A61B 5/18* (2006.01)
(Continued)

(52) U.S. Cl.
CPC ............ *A61B 5/7207* (2013.01); *A61B 5/024* (2013.01); *A61B 5/0205* (2013.01);
(Continued)

(58) Field of Classification Search
CPC ..... A61B 5/4806; A61B 5/4809; A61B 5/024; A61B 5/282; A61B 5/18; A61B 5/7278;
(Continued)

(56) References Cited

U.S. PATENT DOCUMENTS

| 8,768,442 B2 * | 7/2014 | Nakano .............. A61B 5/0468 600/513 |
| 2010/0217137 A1 | 8/2010 | Kanai et al. |

(Continued)

FOREIGN PATENT DOCUMENTS

| JP | 7-124140 | 5/1995 |
| JP | 07124140 A * | 5/1995 |

(Continued)

OTHER PUBLICATIONS

Japanese Office Action dated Mar. 12, 2019 from Japanese Patent Application No. 2015-184290, 7 pages.

*Primary Examiner* — Meredith Weare
(74) *Attorney, Agent, or Firm* — Staas & Halsey LLP

(57) ABSTRACT

A drowsiness detection device includes a memory; and a processor coupled to the memory and the processor configured to calculate a respiration variation period based on heartbeat interval data which is generated based on data that is obtained from a heartbeat sensor; predict a subsequent period structure of the respiration variation based on the calculated respiration variation period; determine whether or not an abnormal signal is mixed in the heartbeat interval data by comparing the heartbeat interval data during sequential update and the predicted subsequent period structure; and replace the respiration variation period which corresponds to the heartbeat interval data that includes the abnormal signal with the predicted subsequent period structure in a case where it is determined that the abnormal signal is mixed.

6 Claims, 16 Drawing Sheets

(51) Int. Cl.
   *A61B 5/00*       (2006.01)
   *A61B 5/0205*     (2006.01)
   *A61B 5/08*       (2006.01)
   *A61B 5/0245*     (2006.01)

(52) U.S. Cl.
   CPC ........ *A61B 5/02405* (2013.01); *A61B 5/0816* (2013.01); *A61B 5/18* (2013.01); *A61B 5/7278* (2013.01); *A61B 5/7282* (2013.01); *A61B 5/742* (2013.01); *A61B 5/0245* (2013.01); *A61B 5/02416* (2013.01)

(58) Field of Classification Search
   CPC ..... A61B 5/0205; A61B 5/742; A61B 5/0816; A61B 5/02416; A61B 5/0245; A61B 5/7282
   See application file for complete search history.

(56) References Cited

U.S. PATENT DOCUMENTS

| | | | |
|---|---|---|---|
| 2012/0192874 A1* | 8/2012 | Bolea | A61N 1/3601 128/848 |
| 2012/0197091 A1* | 8/2012 | Nakano | A61B 5/0245 600/301 |
| 2017/0071489 A1* | 3/2017 | Presura | A61B 5/721 |

FOREIGN PATENT DOCUMENTS

| | | |
|---|---|---|
| JP | 2003-339651 | 12/2003 |
| JP | 2006-81840 | 3/2006 |
| JP | 2013-123524 | 6/2013 |
| JP | 2015-80624 | 4/2015 |
| WO | 2008/149559 A1 | 12/2008 |

* cited by examiner

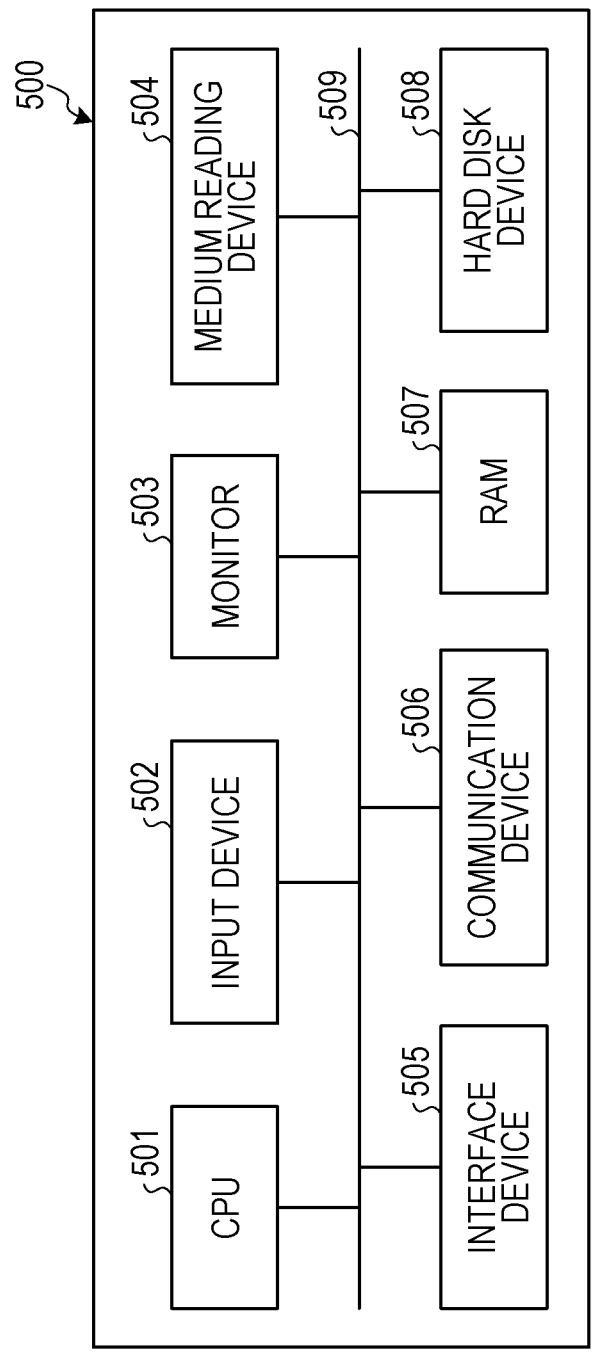

DROWSINESS DETECTION DEVICE, DROWSINESS DETECTION METHOD, AND COMPUTER-READABLE RECORDING MEDIUM STORING PROGRAM FOR DROWSINESS DETECTION

CROSS-REFERENCE TO RELATED APPLICATION

This application is based upon and claims the benefit of priority of the prior Japanese Patent Application No. 2015-184290, filed on Sep. 17, 2015, the entire contents of which are incorporated herein by reference.

FIELD

The embodiment discussed herein is related to a drowsiness detection device, a drowsiness detection method, and a computer-readable recording medium storing program for drowsiness detection.

BACKGROUND

Heart rate fluctuation or heart rate variability is utilized as a method for determining a drowsiness level of a subject. For example, the method based on the heart rate fluctuation is used to continuously obtain a fixed number or more of heartbeat interval values, to calculate spectral density by frequency converting the obtained data row, and to determine the drowsiness level of the subject. It is possible to calculate the heartbeat interval between R waves, which have the largest amplitude in each heartbeat. The heartbeat interval is able to be calculated using a time interval of two R waves which are, for example, adjacent heartbeats, and is referred to as an R-R interval (RRI).

It is suggested to use a drowsiness detection device based on the technique for monitoring a vehicle driver. However, when the drowsiness detection device obtains the heartbeat signal of the driver in order to generate heartbeat interval data, there is a case where noise due to influence of vehicle vibration and the like is generated to result in an electrocardiograph signal including noise. In a case where the drowsiness detection device obtains the heartbeat interval data including noise, reliability of fluctuation analysis, which is carried out to convert the heartbeat interval data to a drowsiness value, is reduced because a target fluctuation component is reduced. When detecting noise, the drowsiness detection device specifies a range of heartbeat interval data which includes the noise, and continues calculation of the drowsiness value while correcting the fluctuation component.

Japanese Laid-open Patent Publication Nos. 2006-81840, 7-124140, 2003-339651, and 2013-123524, and International Publication Pamphlet No. 2008/149559 are examples of the related art.

SUMMARY

According to an aspect of the invention, a drowsiness detection device includes a memory and a processor coupled to the memory and the processor configured to calculate a respiration variation period based on heartbeat interval data which is generated based on data that is obtained from a heartbeat sensor; predict a subsequent period structure of the respiration variation based on the calculated respiration variation period; determine whether or not an abnormal signal is mixed in the heartbeat interval data by comparing the heartbeat interval data during sequential update and the predicted subsequent period structure; and replace the respiration variation period which corresponds to the heartbeat interval data that includes the abnormal signal with the predicted subsequent period structure in a case where it is determined that the abnormal signal is mixed.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 18 is a diagram illustrating an example of a computer which executes a drowsiness detection program.

DESCRIPTION OF EMBODIMENTS

In the related technology, when heartbeat interval data is cut out prior to noise mixing after the noise is detected, and the fluctuation component is corrected by replacing the range of the heartbeat interval data which includes noise, there are cases where an analysis stop state of approximately 20 seconds is generated in order to have consistency between the replaced data and data before and after the replaced data. In this case, it is difficult to perform an update of the drowsiness value in real time.

Accordingly, it is desired to provide a drowsiness detection device, a drowsiness detection method, and a computer-readable recording medium storing program for drowsiness detection which are able to secure continuity of a drowsiness estimate.

With reference to the drawings, embodiments of a drowsiness detection device, a drowsiness detection method, and a computer-readable recording medium storing program for drowsiness detection which are the disclosure of the present application will be described below in detail. Here, the disclosed techniques are not limited to the present embodiments. In addition, the embodiments described below may be appropriately combined within a consistent scope.

First Embodiment

Figure 1:
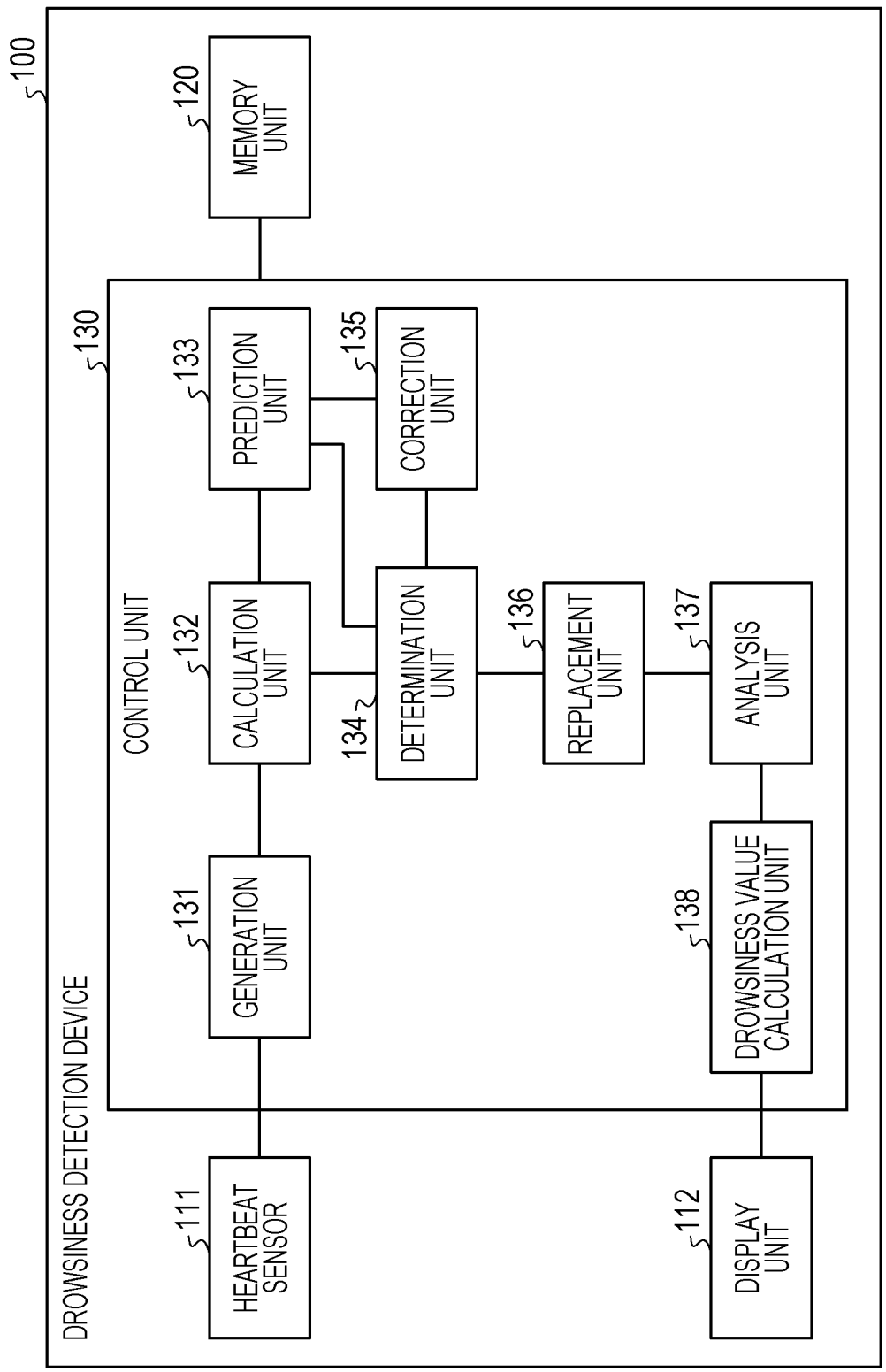
FIG. 1 is a block diagram illustrating an example of a configuration of a drowsiness detection device of a first embodiment.

FIG. 1 is a block diagram illustrating an example of a configuration of a drowsiness detection device of a first embodiment. For example, a drowsiness detection device 100 in FIG. 1 is provided in a vehicle and a heartbeat sensor electrode thereof is mounted on a driver of the vehicle to obtain a heartbeat signal. The drowsiness detection device 100 calculates a respiration variation period based on the heartbeat interval data which is generated based on the data that is obtained from the heartbeat sensor. In addition, the drowsiness detection device 100 predicts a subsequent period structure of respiration variation based on the calculated respiration variation period. The drowsiness detection device 100 determines whether or not an abnormal signal is mixed in the heartbeat interval data by comparing the heartbeat interval data during sequential update and the predicted subsequent period structure. Here, for example, the abnormal signal is noise. In a case where the drowsiness detection device 100 determines that the abnormal signal is mixed, the respiration variation period which corresponds to the heartbeat interval data including the abnormal signal is replaced with the predicted subsequent period structure. The drowsiness detection device 100 carries out spectral analysis on heartbeat interval data which includes the replaced subsequent period structure, and calculates the drowsiness value based on the analysis result. Thereby, it is possible for the drowsiness detection device 100 to secure continuity of a drowsiness estimate.

Next, the configuration of the drowsiness detection device 100 will be described. As illustrated in FIG. 1, the drowsiness detection device 100 includes a heartbeat sensor 111, a display unit 112, a memory unit 120, and a control unit 130. Here, it does not matter even if the drowsiness detection device 100 includes various functional units which include a known computer other than the functional unit that is illustrated in FIG. 1, and for example, includes a functional unit such as various input devices or audio output devices.

The heartbeat sensor 111 detects the heartbeat signal of the subject. For example, the heartbeat sensor 111 obtains the heartbeat signal of the subject from each electrode potential difference using the electrodes which are in contact with the subject. Here, for example, the electrodes which are used by the heartbeat sensor 111 corresponds to electrodes which are embedded in a chest belt type or a pair of small devices of a wristwatch type which are mounted on both hands. The heartbeat sensor 111 outputs the detected heartbeat signal data to the control unit 130 as the heartbeat signal data.

In addition, for example, the heartbeat sensor 111 may be configured to obtain a pulse wave by measuring blood flow at an earlobe and the like of the subject using light. A detection unit of the heartbeat sensor 111 is an optical type when the pulse wave is obtained and is able to use the wristwatch type or a wrist band type of a reflective type, an ear clip type of a reflective type or a transmissive type.

Figure 2:
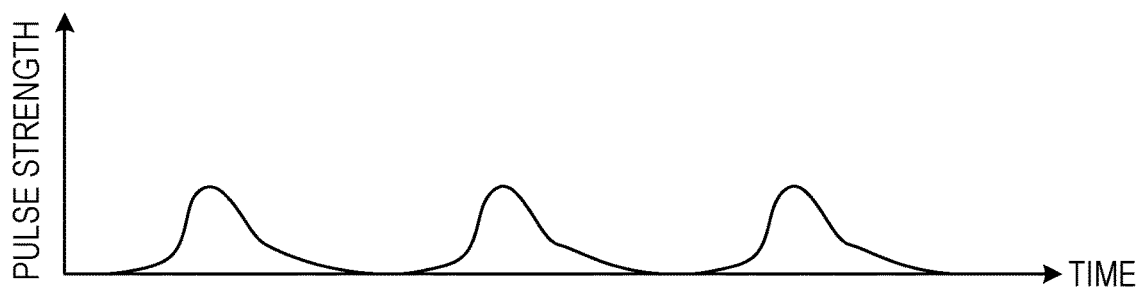
FIG. 2 is a diagram illustrating an example of pulse data.

Referring to FIG. 2, there will be described the signal which is detected by the heartbeat sensor 111. Here, in an example below, an example is described of acquiring the pulse wave, but is similar to the case of the heartbeat signal. FIG. 2 is a diagram illustrating an example of pulse data. As illustrated in FIG. 2, the pulse data indicates pulse strength of each time. In FIG. 2, a vertical axis is an axis which indicates pulse strength, and a horizontal axis is an axis which indicates time.

Returning to the explanation in FIG. 1, the display unit 112 is a display device for displaying various kinds of information. For example, the display unit 112 is realized by a liquid crystal display or the like as the display device. The display unit 112 displays various display screen images which are input from the control unit 130. For example, a warning screen according to the drowsiness value, and a display screen image which represents various messages and the like are given as examples of the various display screen images.

The memory unit 120 is realized by a storage device such as a semiconductor memory device such as a random access memory (RAM) or a flash memory, a hard disk, or an optical disc. The memory unit 120 stores information which is used in a process by the control unit 130. The stored information is, for example, a respiration variation model and the like which includes the predicted subsequent period structure.

A central processing unit (CPU) or a micro processing unit (MPU), as an example of a processor that performs various control and arithmetic operations, executes a program stored in the storage device using the RAM as an operation region, and the control unit 130 is realized. In addition, for example, the control unit 130 may be realized by an integrated circuit such as an application specific integrated circuit (ASIC) or a field programmable gate array (FPGA). The control unit 130 includes a generation unit 131, a calculation unit 132, a prediction unit 133, a determination unit 134, a correction unit 135, a replacement unit 136, an analysis unit 137, and a drowsiness value calculation unit 138, and realizes or executes a function or action of information processing which is described below. Here, the internal configuration of the control unit 130 is not limited to the configuration illustrated in FIG. 1, and may be another configuration as long as the configuration performs the information processing described later.

The generation unit 131 generates heartbeat interval data based on the heartbeat signal data which is obtained from the heartbeat sensor 111. When starting input of the heartbeat signal data from the heartbeat sensor 111, the generation unit 131 starts generation of the heartbeat interval data (hereinafter referred to as RRI data) in which time intervals of two R waves that are of adjacent heartbeats and an R wave detection time are associated. The generation unit 131 starts output of generated RRI data to the calculation unit 132. Here, since the heartbeat signal data is sequentially input to the generation units 131, the generation unit 131 sequentially updates and outputs the RRI data.

Figure 3:
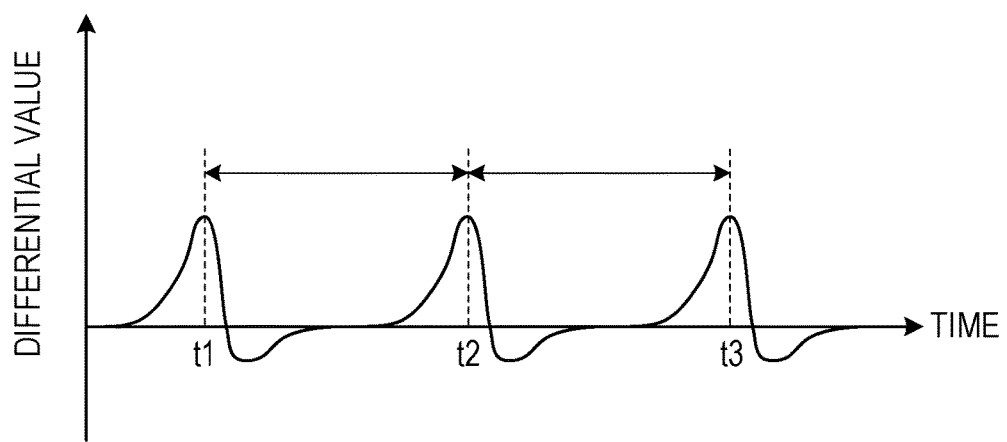
FIG. 3 is a diagram illustrating an example of differential pulse data.

In a case where the pulse wave is used, the generation unit 131 generates differential pulse data by differentiating the pulse data which is obtained from the heartbeat sensor 111. FIG. 3 is a diagram illustrating an example of differential pulse data. In FIG. 3, the vertical axis is an axis which indicates a differential value of the pulse data, and the horizontal axis is an axis which indicates time. The generation unit 131 scans the differential pulse data, and specifies time at which the differential value is locally maximized. In the example illustrated in FIG. 3, in time t1, t2, and t3, the differential value is locally maximized. The generation unit 131 calculates the interval from an amplitude peak to the subsequent amplitude peak as peak-peak-interval (PPI) data. The calculated PPI data may be used as the heartbeat signal in the same manner as the RRI data, and in the explanation below, may use the PPI data in which the RRI data is used.

Returning to the explanation in FIG. 1, when receiving the RRI data from the generation unit 131, the calculation unit 132 calculates the respiration variation period. The calculation unit 132 generates the RRI data row in which each set of RRI data is plotted on a time axis, that is, a respiration variation graph, and calculates the respiration variation period based on the RRI data row. For example, the calculation unit 132 calculates a time between adjacent local maximum points within the RRI data row as one period. That is, the calculation unit 132 calculates the local maximum points and the local minimum points within an integrated interval of the RRI data row, a time between adjacent local maximum points is taken as one period of the respiration variation, and calculates the period and amplitude. Here, in the explanation below, a set of the calculated period and amplitude is expressed as the respiration variation period. The calculation unit 132 outputs the period of the calculated respiration variation and the RRI data row to the prediction unit 133. In addition, the calculation unit 132 starts output of the RRI data row to the determination unit 134.

The heartbeat interval data (RRI data) will be described. The heartbeat interval data varies according to respiration, that is, varies due to adjustment of autonomic nerves. For example, as elements of the variation, there are heartbeat blood pressure variation which is referred to as Mayer Wave Sinus Arrhythmia (MWSA) and Respiratory Sinus Arrhythmia which is referred to as Respiratory Sinus Arrhythmia (RSA). The respiration variation period in the heartbeat interval data includes a component in a low frequency side (LF) of around 0.05 Hz to 0.15 Hz due to MWSA and a component in a high frequency side (HF) of around 0.15 Hz to 0.4 Hz due to RSA.

That is, the heartbeat interval is determined by a balance between a signal which increases the heartbeat through the sympathetic nervous system and a signal which decreases the heartbeat through the parasympathetic nervous system. The heartbeat interval is determined by blocking control of the parasympathetic nervous system at the start of inspiration from a mechanism of the heartbeat variation due to respiration dynamism, comes to be a heartbeat elevated state upon control of the sympathetic nervous system, and at the start of exhalation restores control of the parasympathetic nervous system, and the heartbeat is reduced. That is, the heartbeat interval is increased and reduced according to the respiration operation. In addition, when the heartbeat is generated in the same manner in enhancement of the heartbeat and detection by an arterial baroreceptor of an internal pressure increase due to large inhalation activity, control of the sympathetic nervous system from the heartbeat epicenter through a blood pressure adjustment mechanism and control in which the number of heartbeats is reduced through enhancement of the parasympathetic nervous system are performed.

A change of the heartbeat interval is reflectively performed in conjunction with periodic respiratory activity, and drowsiness estimation is performed in relation to the frequency distribution. For this reason, it is preferable to update the heartbeat interval data in each respiration period in the drowsiness estimate. In addition, the local maximum point in the heartbeat interval data corresponds to a heartbeat state controlled through the parasympathetic nervous system, and the local minimum point in the heartbeat interval data corresponds to a heartbeat state controlled through the sympathetic nervous system. That is, the local maximum point represents an inspiration start point and has the highest correlation with a state in which the parasympathetic nervous system and the sympathetic nervous system function. In addition, the local minimum point represents an exhalation start point and has the highest correlation with a state in which only the sympathetic nervous system functions. That is, it is preferable to define the drowsiness by using the trend of local maximum points in the heartbeat interval data.

The periodic structure between the inspiration and the respiration becomes unclear under a situation in which a breath is taken, a situation in which sympathetic nerve is elevated by active activity such as a speech response, or a situation such as swallowing or yawn which causes a reflex action of the pressure sensitive receptor. That is, in such a case, it is considered that accompanying a reverse-phase operation the local minimum point of the heartbeat interval does not necessarily match an exhalation point, and in the subsequent respiration period, returns to the original period.

When receiving the respiration variation period and the RRI data row from the calculation unit 132, the prediction unit 133 predicts the subsequent period structure of respiration variation. The prediction unit 133 performs a signal estimation using a cosine function which starts from a point of a last maximus in the RRI data row based on the past respiration variation period within an integrated interval of the RRI data row and the input respiration variation period, and calculates the respiration variation model to predict the subsequent period structure. In addition, when receiving the corrected respiration variation model from the correction unit 135, the prediction unit 133 predicts the subsequent period structure using the corrected respiration variation model. The prediction unit 133 outputs the respiration variation model which includes the predicted subsequent period structure to the determination unit 134 and the correction unit 135.

When receiving an instruction for correction from a determination unit 134, the prediction unit 133 corrects the respiration variation model by adding a respiration variation of one period in a sequentially updated RRI data row to the integrated interval by removing the oldest one period of the respiration variation in the integrated interval.

Figure 4:
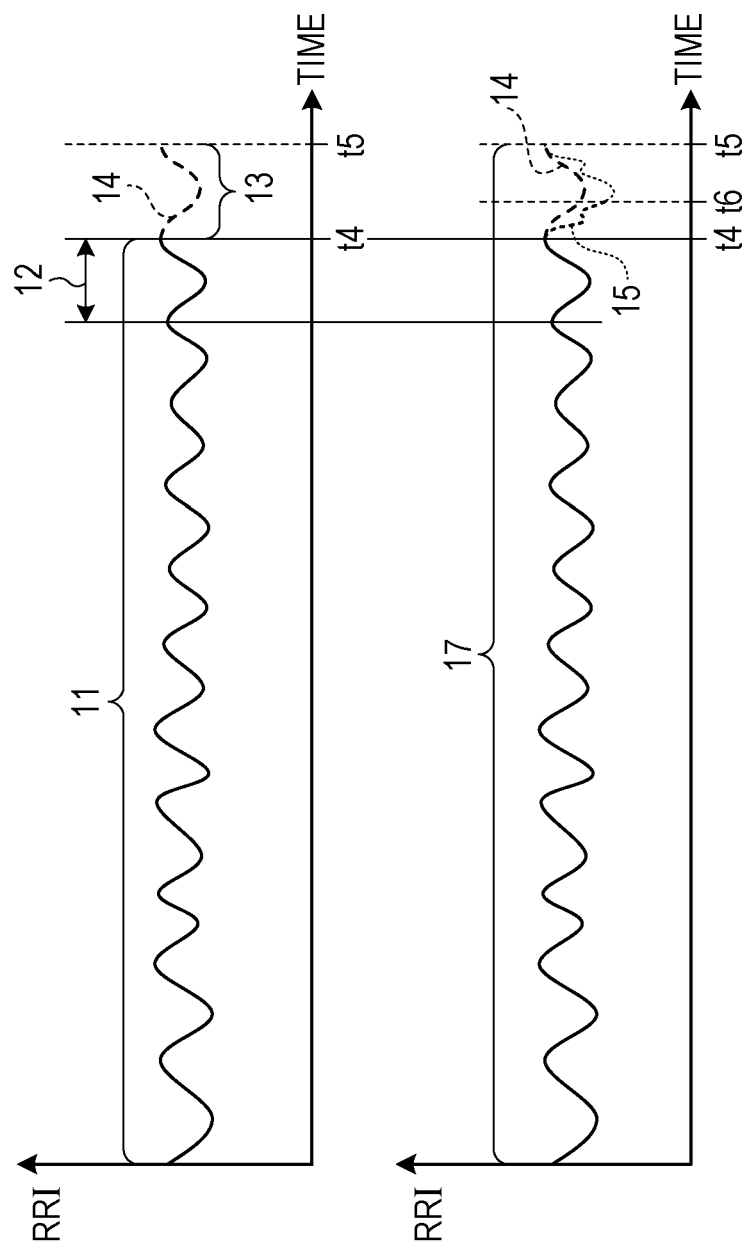
FIG. 4 is a diagram illustrating an example of sequential prediction correction.

Referring to FIG. 4, the subsequent period structure prediction will be described. FIG. 4 is a diagram illustrating an example of sequential prediction correction. As illustrated in FIG. 4, in the RRI data row as the respiration variation graph, the prediction unit 133 predicts a period structure 14 in a subsequent period 13 based on the respiration variation periods in a determined interval 11. One period of the respiration variation in the determined interval 11, for example, is the interval 12. When the current time is a time t4, the prediction unit 133 performs the signal estimate using the cosine function which starts from the first last local maximum point in the interval 11, and predicts the period structure 14 in the period 13 until one period structure future time t5, that is, from the time t4 until the time t5. In addition, an interval 17 illustrated in FIG. 4 is an interval which includes the predicted period structure 14. Here, a waveform 15 illustrated in FIG. 4 is based on a measured value of the RRI data row in a time t6.

Returning to the explanation for FIG. 1, when receiving the RRI data row from the calculation unit 132 and the respiration variation model from the prediction unit 133, the determination unit 134 compares the RRI data row during sequential update and the predicted subsequent period structure of the respiration variation model. In the comparison result, the determination unit 134 determines whether or not an abnormal signal is mixed in the RRI data row. For example, the determination unit 134 determines that the abnormal signal is mixed in a case where the period structure of the RRI data row during being sequentially updated and the subsequent period structure are different from each other by ±5% or more. In the example in FIG. 4, it is determined that the abnormal signal is mixed in a case where the waveform 15 is, for example, different by ±5% or more from the predicted period structure 14. In a case where the determination unit 134 determines that the abnormal signal is mixed, the determination unit 134 outputs the determination result in which the abnormal signal is mixed, the RRI data row during being sequentially updated, and the respiration variation model to the replacement unit 136.

In addition, in a case where the determination unit 134 determines that the abnormal signal is not mixed, the determination unit 134 determines whether or not correction is carried out so that the local minimum points are matched. Here, the determination unit 134 determines whether or not correction is carried out such that the local minimum points are matched with reference to a set value which indicates a correction propriety which is set in advance by a user. In a case where the determination unit 134 corrects so that the local minimum points are matched, the determination unit 134 outputs the correction instruction and the RRI data row during sequential update to the correction unit 135. That is, in a case where the determination unit 134 corrects such that the local minimum points are matched, the determination unit 134 compares the RRI data row during sequential update and the predicted sequential period structure of the respiration variation model which is corrected by the correction unit 135. In addition, the determination unit 134 outputs, to the replacement unit 136, the determination result in which the abnormal signal is not mixed, the RRI data row during sequential update, and the respiration variation model.

In a case where the determination unit 134 does not correct such that the local minimum points are matched, the determination unit 134 outputs, to the replacement unit 136, the determination result in which the abnormal signal is not mixed, the RRI data row during sequential update, and the respiration variation model.

The determination unit 134 determines whether or not the sequential update for one period of the RRI data row completes. In a case where the sequential update for one period of the RRI data row does not complete, the determination unit 134 continues comparison of the RRI data row and the respiration variation model. In a case where the sequential update for one period of the RRI data row completes, the determination unit 134 outputs the correction instruction to the prediction unit 133 in order that the updated one period is reflected in the respiration variation model.

The respiration variation model is input from the prediction unit 133 to the correction unit 135. In addition, the correction instruction from the determination unit 134 and the RRI data row during sequential update are input in the correction unit 135. When receiving the correction instruction and the RRI data row during sequential updatet, the correction unit 135 shifts and corrects the subsequent period structure of the respiration variation model such that the local minimum point of the sequential period structure of the respiration variation matches the local minimum point of the respiration variation period based on the RRI data row during sequential update. The correction unit 135 outputs the corrected respiration variation model to the prediction unit 133. Here, in a case where a shift amount of the subsequent period structure is, for example, 20% or less of one period, the correction unit 135 does not perform correction of the respiration variation model. In addition, the correction unit 135 may shift and correct the subsequent period structure of the respiration variation model such that the local maximum points are matched in place of the local minimum points.

Figure 5:
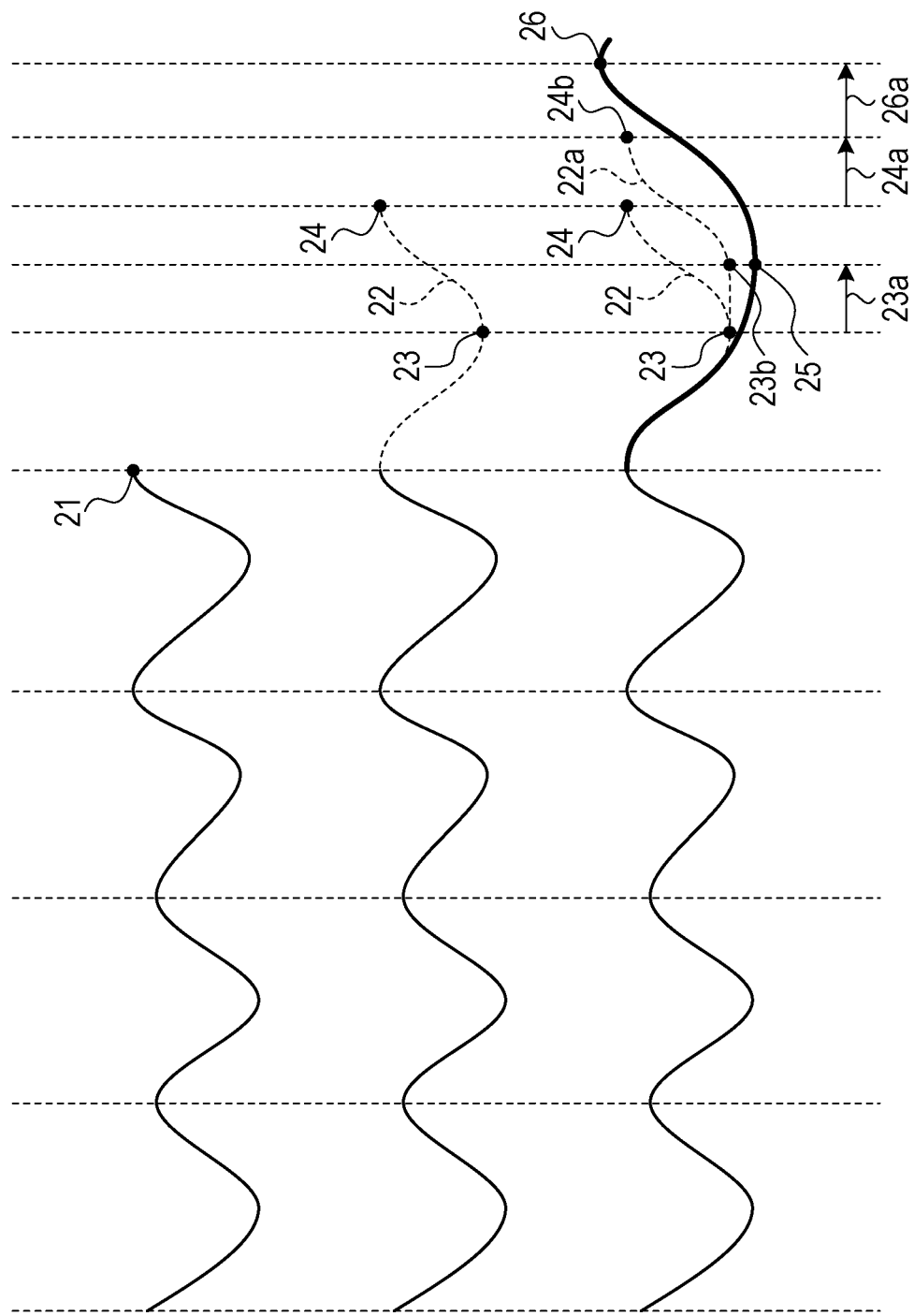
FIG. 5 is a diagram illustrating an example of a period structure shift.

Referring to FIG. 5, an example of the shift of the period structure will be described. FIG. 5 is a diagram illustrating an example of a period structure shift. As illustrated in FIG. 5, in the respiration variation model, a period structure 22 is predicted from a local maximum point 21 of the RRI data row, and a subsequent local minimum point 23 and a local maximum point 24 is predicted. Here, the local minimum point 25 of the actual measured value RRI data row is shifted only by a period 23a from the predicted local minimum point 23. For this reason, the correction unit 135 shifts the predicted local minimum point 23 to a local minimum point 23b by a period 23a. In the same manner, the correction unit 135 shifts the predicted value local maximum point 24 to the local maximum point 24b by a period 24a. That is, the correction unit 135 shifts the subsequent period structure 22 of the respiration variation model and corrects to a period structure 22a such that the correction unit 135 matches the local minimum point 23 of the subsequent period structure with the minimum point 25 of the respiration variation period based on the RRI data row during sequential update. Here, in the example in FIG. 5, at a time of the subsequent local maximum point 24b after shifting, since there occurs a difference between the corrected period structure 22a and the measured RRI data row, the local maximum point 24b may be shifted by a period 26a to a local maximum point 26 of the actual measured value RRI data row. That is, the correction unit 135 corrects the respiration variation model such that the respiration variation model follows the respiration variation period according to the RRI data row during sequential update.

Returning to the explanation for FIG. 1, the determination result of the abnormal signal mixing from the determination unit 134, the RRI data row during sequential update, and the respiration variation model are input in the replacement unit 136. In a case where the replacement unit 136 receives the determination result noticing that the abnormal signal is mixed in the RRI data row, the replacement unit 136 replaces the respiration variation period which corresponds to the RRI data row during sequential update including the abnormal signal with the predicted subsequent period structure of the respiration variation model. That is, when the replacement unit 136 detects that the abnormal signal is mixed in the RRI data row, the RRI data row of one period of the respiration variation period including the abnormal signal is replaced with the period structure of the respiration variation model by the replacement unit 136. In the example illustrated in FIG. 4, the replacement unit 136 replaces one period (t4 to t5) of the waveform 15 which includes the abnormal signal with the predicted period structure 14. The replacement unit 136 output, to the analysis unit 137, the RRI data row of the period structure of the respiration variation model which is obtained by replacing one period of the respiration variation including the abnormal signal.

When receiving the determination result that the abnormal signal is not mixed, the replacement unit 136 carries out resampling on one period of the RRI data row sequentially updated. The replacement unit 136 outputs the RRI data row which includes one period of resampled RRI data row to the analysis unit 137.

When receiving the RRI data row from the replacement unit 136, the analysis unit 137 converts the received RRI data row to spectral density (PSD) data using an auto regressive (AR) model. The spectral density data is data which indicates a relationship between the frequency and spectral density. Here, an example is illustrated in which the analysis unit 137 converts the RRI data row to the spectral density data using the AR model. A Fourier transform may be used for converting the RRI data row to the spectral density data. The analysis unit 137 outputs the obtained spectral density data to the drowsiness value calculation unit 138.

Figure 6:
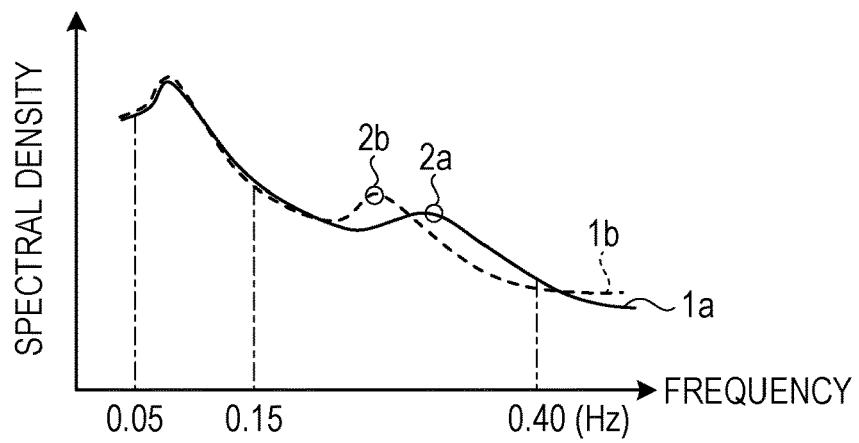
FIG. 6 is a diagram illustrating an example of spectral density data.

FIG. 6 is a diagram illustrating an example of spectral density data. In FIG. 6, the vertical axis is an axis which corresponds to spectral density, and the horizontal axis is an axis which corresponds to frequency. For example, a graph 1a indicates a relationship between the spectral density and frequency of the RRI data row in a time TT1. For example, a graph 1b indicates a relationship between the spectral density and frequency of the RRI data row in a time TT2.

For example, a region is set to a low frequency region from frequency 0.05 Hz to 0.15 Hz, and a region is set to a high frequency region from frequency 0.15 Hz to 0.40 Hz. When classifying the region of such a frequency, the RSA in the graph 1a is 2a, and RSA in the graph 1b is 2b. In the RSA, a graph which indicates a relationship between the spectral density and frequency of the RRI data indicates the peak on a high frequency side.

Returning to the explanation in FIG. 1, when receiving the spectral density data from the analysis unit 137, the drowsiness value calculation unit 138 determines drowsiness of the subject based on the relationship between the spectral density and frequency which corresponds to RSA. In a case where the RSA changes with time from higher to lower in frequency and from larger to smaller in spectral density, the drowsiness value calculation unit 138 determines that awareness or alertness of the subject is reduced. For example, in the example in FIG. 6, it is assumed that the graph 1b has been obtained after the graph 1b. The comparison of the RSA 2b with RSA 2a with respect to frequencies and spectral densities thereof indicates that RSA 2a moves figuratively to RSA 2b such that the frequency reduces and the spectral density increases. In this case, the drowsiness value calculation unit 138 determines that awareness or alertness of the subject is reduced and determines a doze state.

Figure 7:
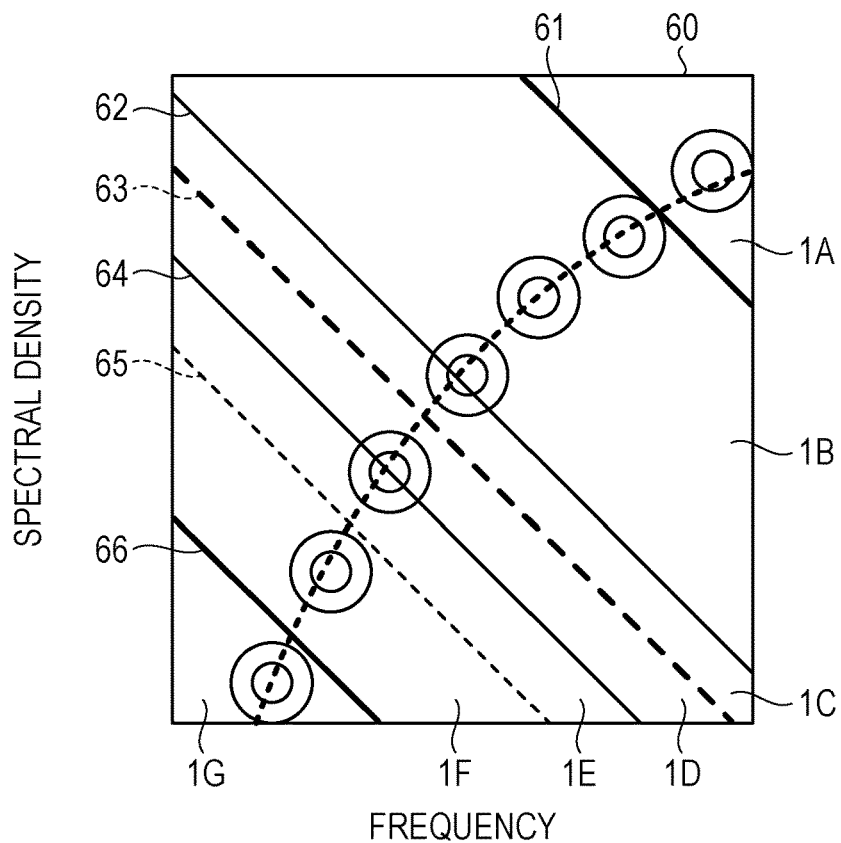
FIG. 7 is a diagram for describing a drowsiness level.

From the relationship between the frequency and spectral density of RSA, the drowsiness value calculation unit 138 determines a drowsiness value, that is, a drowsiness level. The drowsiness level will be explained with referenced to a diagram illustrated in FIG. 7. In FIG. 7, the vertical axis corresponds to spectral density, and the horizontal axis corresponds to frequency. The value of the spectral density decreases along the vertical axis toward the upper side. The value of the frequency decreases along the horizontal axis toward the right side. That is, in FIG. 7, as a coordinate point moves toward the left below in the diagram, alertness corresponding to the coordinate point is reduced which has the meaning that the drowsiness level increases.

For example, the drowsiness value calculation unit 138 sets, based on threshold data of the drowsiness level set in advance, thresholds 61, 62, 63, 64, 65, and 66 with respect to a graph 60 which indicates the relationship between spectral density and frequency. In the threshold data, for example, each threshold holds information which defines the relationship between frequency and spectral density.

For example, the drowsiness value calculation unit 138 divides, into a plurality of regions 1A to 1G, the graph 60 which indicates the relationship between spectral density and frequency according to the thresholds 61 to 66. In a case where the relationship between spectral density and frequency is included in the region 1A, the drowsiness value calculation unit 138 determines the drowsiness level of the subject as a drowsiness level 1. In a case where the relationship between spectral density and frequency is included in the region 1B, the drowsiness value calculation unit 138 determines the drowsiness level of the subject as a drowsiness level 2. In a case where the relationship between spectral density and frequency is included in the region 1C, the drowsiness value calculation unit 138 determines the drowsiness level of the subject as a drowsiness level 3. In a case where the relationship between spectral density and frequency is included in the region 1D, the drowsiness value calculation unit 138 determines the drowsiness level of the subject as a drowsiness level 4. In a case where the relationship between spectral density and frequency is included in the region 1E, the drowsiness value calculation unit 138 determines the drowsiness level of the subject as a drowsiness level 5. In a case where the relationship between spectral density and frequency is included in the region 1F, the drowsiness value calculation unit 138 determines the drowsiness level of the subject as a drowsiness level 6. In a case where the relationship between spectral density and frequency is included in the region 1G, the drowsiness value calculation unit 138 determines the drowsiness level of the subject as a drowsiness level 7.

In a case where the drowsiness value calculation unit 138 determines the drowsiness level of the subject and the drowsiness level is a predetermined level or more, a warning is provided to the subject. In a case where the drowsiness level is 4 or more, for example, the drowsiness value calculation unit 138 displays a warning screen on the display unit 112, and outputs a warning sound from a loudspeaker which is not illustrated in the drawings.

In addition, for example, the drowsiness value calculation unit 138 determines whether or not a drowsiness detection process is set to be ended based on an input from a switch which is not illustrated in the drawings. For example, when the subject ends driving of an automobile and the switch which is not illustrated in the drawings is pressed by the subject, the drowsiness value calculation unit 138 ends the drowsiness detection process.

Figure 8:
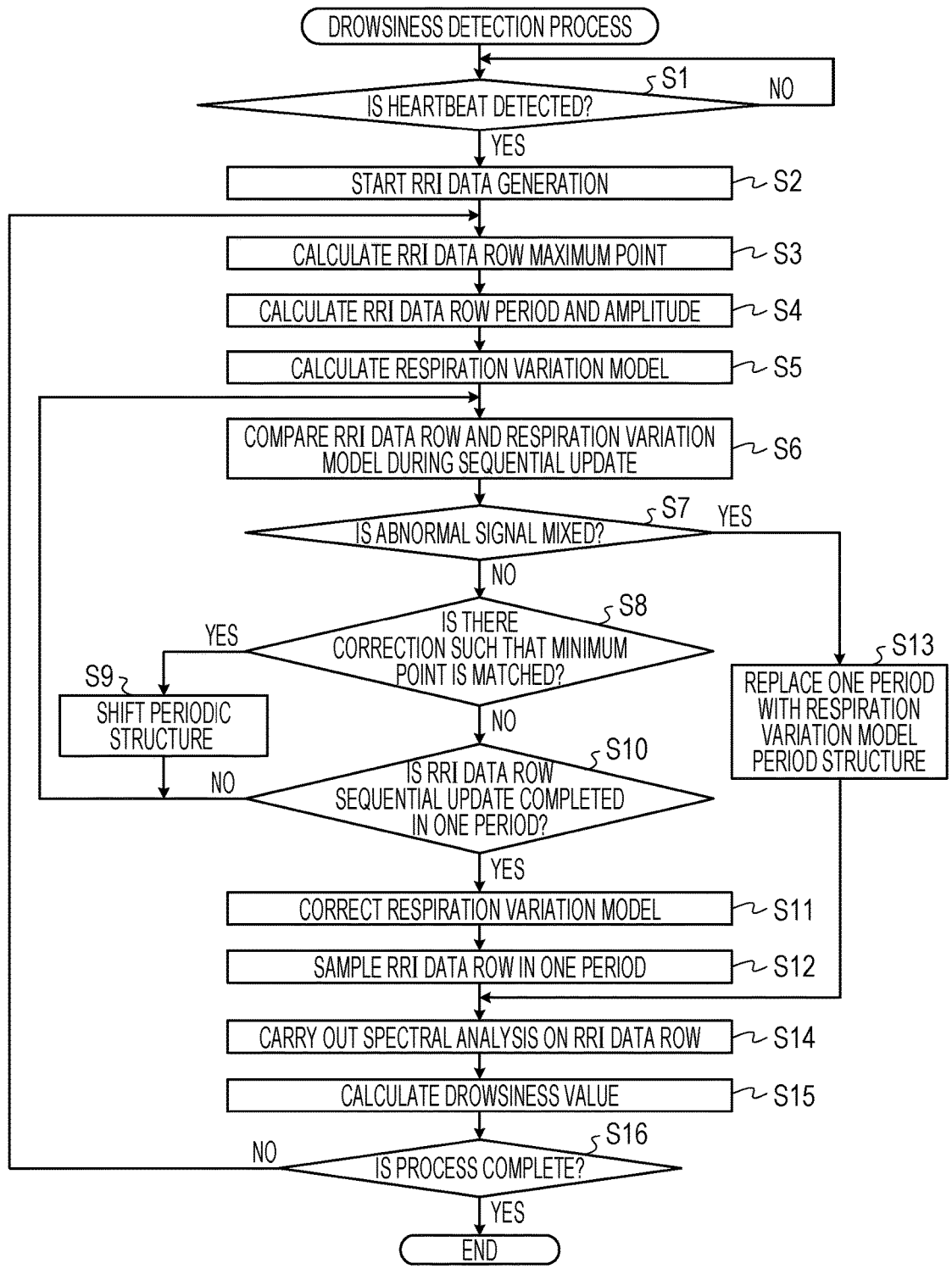
FIG. 8 is a flow chart illustrating an example of a drowsiness detection process of the first embodiment.

Next, the operation of the drowsiness detection device 100 of the first embodiment will be described below. FIG. 8 is a flow chart illustrating an example of the drowsiness detection process of the first embodiment.

The generation unit 131 determines whether or not the heartbeat is detected, that is, whether or not input of the heartbeat signal data from the heartbeat sensor 111 starts (step S1). In a case where the heartbeat is not detected (step S1: NO), the generation unit 131 puts heartbeat detection in standby. In a case where the heartbeat is detected (step S1: YES), the generation unit 131 starts generation of the RRI data (step S2). The generation unit 131 starts output of generated RRI data with respect to the calculation unit 132.

When receiving the RRI data from the generation unit 131, the calculation unit 132 generates the RRI data row such that each set of RRI data is plotted at a coordinate value on the time axis corresponding to a time at which the set of RRI data is detected. The calculation unit 132 calculates the local maximum point of the generated RRI data row (step S3). The calculation unit 132 determines one between local maximum points as one period of the respiration variation, and calculates the respiration variation period, that is, the period and amplitude of the RRI data row (step S4). The calculation unit 132 outputs the period of the calculated respiration variation and the RRI data row to the prediction unit 133. In addition, the calculation unit 132 starts output of the RRI data row to the determination unit 134.

When receiving the respiration variation period and the RRI data row are input from the calculation unit 132, the prediction unit 133 calculates the respiration variation model and predicts the subsequent period structure (step S5). The prediction unit 133 outputs the respiration variation model which includes the predicted subsequent period structure to the determination unit 134 and the correction unit 135.

When starting to receive the RRI data row from the calculation unit 132 and receiving the respiration variation model from the prediction unit 133, the determination unit 134 compares the RRI data row during sequential update and the predicted subsequent period structure of the respiration variation model (step S6). In the comparison result, the determination unit 134 determines whether or not the abnormal signal is mixed in the RRI data row (step S7). In a case where the determination unit 134 determines that the abnormal signal is not mixed (step S7: NO), the determination unit 134 determines whether or not correction is carried out such that the local minimum points is matched (step S8).

In a case where a correction is performed by matching the local minimum points (step S8: YES), the determination unit 134 outputs the correction instruction and the RRI data row during sequential update to the correction unit 135. In addition, the determination unit 134 outputs, to the replacement unit 136, the determination result in which the abnormal signal is not mixed, the RRI data row during sequential update, and the respiration variation model. When receiving the correction instruction and the RRI data row during sequential update from the determination unit 134, the correction unit 135 shifts the subsequent period structure of the respiration variation model for correction of the subsequent period structure of the respiration variation model (step S9). The correction unit 135 outputs the corrected respiration variation model to the prediction unit 133, and the process returns to step S6.

In a case where a correction by matching the local minimum points is not performed (step S8: NO), the determination unit 134 outputs the determination result in which the abnormal signal is not mixed, the RRI data row during sequential update, and the respiration variation model to the replacement unit 136. The determination unit 134 determines whether or not the sequential update for one period of the RRI data row completes (step S10). In a case where the determination unit 134 does not complete the sequential update for one period of the RRI data row (step S10: NO), the process returns to step S6.

In a case where the sequential update for one period of the RRI data row completes (step S10: YES), the determination unit 134 outputs the correction instruction to the prediction unit 133. When receiving the correction instruction from a determination unit 134, the prediction unit 133 corrects the respiration variation model in order that the updated one period is reflected in the respiration variation model (step S11).

When receiving, from the determination unit 134, the determination result that the abnormal signal is not mixed is input, the replacement unit 136 carries out resampling on the RRI data row of one period in which the RRI data row is sequentially updated (step S12). The replacement unit 136 outputs, to the analysis unit 137, the RRI data row which includes the RRI data row of one period in which resampling is carried out.

In a case where the determination unit 134 determines that the abnormal signal is mixed (step S7: YES), the determination unit 134 outputs, to the replacement unit 136, the determination result in which the abnormal signal is mixed, the RRI data row during sequential update, and the respiration variation model. When receiving, from the determination unit 134, the determination result that the abnormal signal is mixed, the replacement unit 136 replaces, with the period structure of the respiration variation model, the RRI data row of one period of the respiration variation period which includes the abnormal signal (step S13). The replacement unit 136 output, to the analysis unit 137, the RRI data row which is obtained by replacing RRI data of one period of the respiration variation including the abnormal signal with the period structure of the respiration variation model.

When receiving the RRI data row from the replacement unit 136, the analysis unit 137 carries out spectral analysis on the RRI data row (step S14). That is, the analysis unit 137 converts the RRI data row to the spectral density data. The analysis unit 137 outputs the spectral density data to the drowsiness value calculation unit 138. When receiving the spectral density data from the analysis unit 137, the drowsiness value calculation unit 138 calculates the drowsiness value, that is, the drowsiness level (step S15). In a case where the drowsiness level of the subject is a predetermined level or more, the drowsiness value calculation unit 138 displays the warning screen on the display unit 112, and outputs the warning sound from a loudspeaker which is not illustrated in the drawings.

The drowsiness value calculation unit 138 determines whether or not to end the drowsiness detection process (step S16). In the drowsiness value calculation unit 138, in a case where the drowsiness detection process does not end (step S16: NO), the process returns to step S3. In a case where the drowsiness detection process ends (step S16: YES), the drowsiness value calculation unit 138 stops each process unit within the control unit 130, and ends the drowsiness detection process. Thereby, it is possible for the drowsiness detection device 100 to secure continuity of a drowsiness estimate. In addition, since the drowsiness detection device 100 is possible to estimate an end of inspiration by using a local minimum point, the drowsiness detection device 100 is able to quickly determine period abnormality. Furthermore, the drowsiness detection device 100 may perform the correction and the spectral calculation in real time because the drowsiness detection device 100 corrects the respiration variation model by using a phase shift between local minimum points according to variation in the RRI data row during update. That is, the drowsiness detection device 100 may simultaneously perform a process of determination for mixing of the abnormal signal and a process for replacement to the period structure of the respiration variation model.

In this manner, the drowsiness detection device 100 calculates a respiration variation period based on the heartbeat interval data which is generated based on the data that is obtained from the heartbeat sensor. In addition, the drowsiness detection device 100 predicts a subsequent period structure of respiration variation based on the calculated respiration variation period. In addition, the drowsiness detection device 100 determines whether or not an abnormal signal is mixed in the heartbeat interval data by comparing the heartbeat interval data during sequential update and the predicted subsequent period structure. In addition, in a case where the drowsiness detection device 100 determines that the abnormal signal is mixed, the drowsiness detection device 100 replaces, with the predicted subsequent period structure, the respiration variation period which corresponds to the heartbeat interval data including the abnormal signal. Accordingly, it is possible to secure continuity of the drowsiness estimate.

In addition, the drowsiness detection device 100 calculates, as one period, the respiration variation between local maximum points. In addition, the drowsiness detection device 100 corrects the predicted subsequent period structure by shifting the predicted subsequent period structure such that the local minimum point of the predicted subsequent period structure matches the local minimum point of the respiration variation period obtained from the heartbeat interval data during sequential update, or the local maximum point of the predicted subsequent period structure matches the local maximum point of the respiration variation period. In addition, the drowsiness detection device 100 determines whether or not an abnormal signal is mixed in the heartbeat interval data by comparing the heartbeat interval data during sequential update and the shifted subsequent period structure. The drowsiness detection device 100 adjusts the predicted value of the respiration variation period to the measured value of the respiration variation period to automatically carry out period adjustment of the respiration variation.

Second Embodiment

Figure 9:
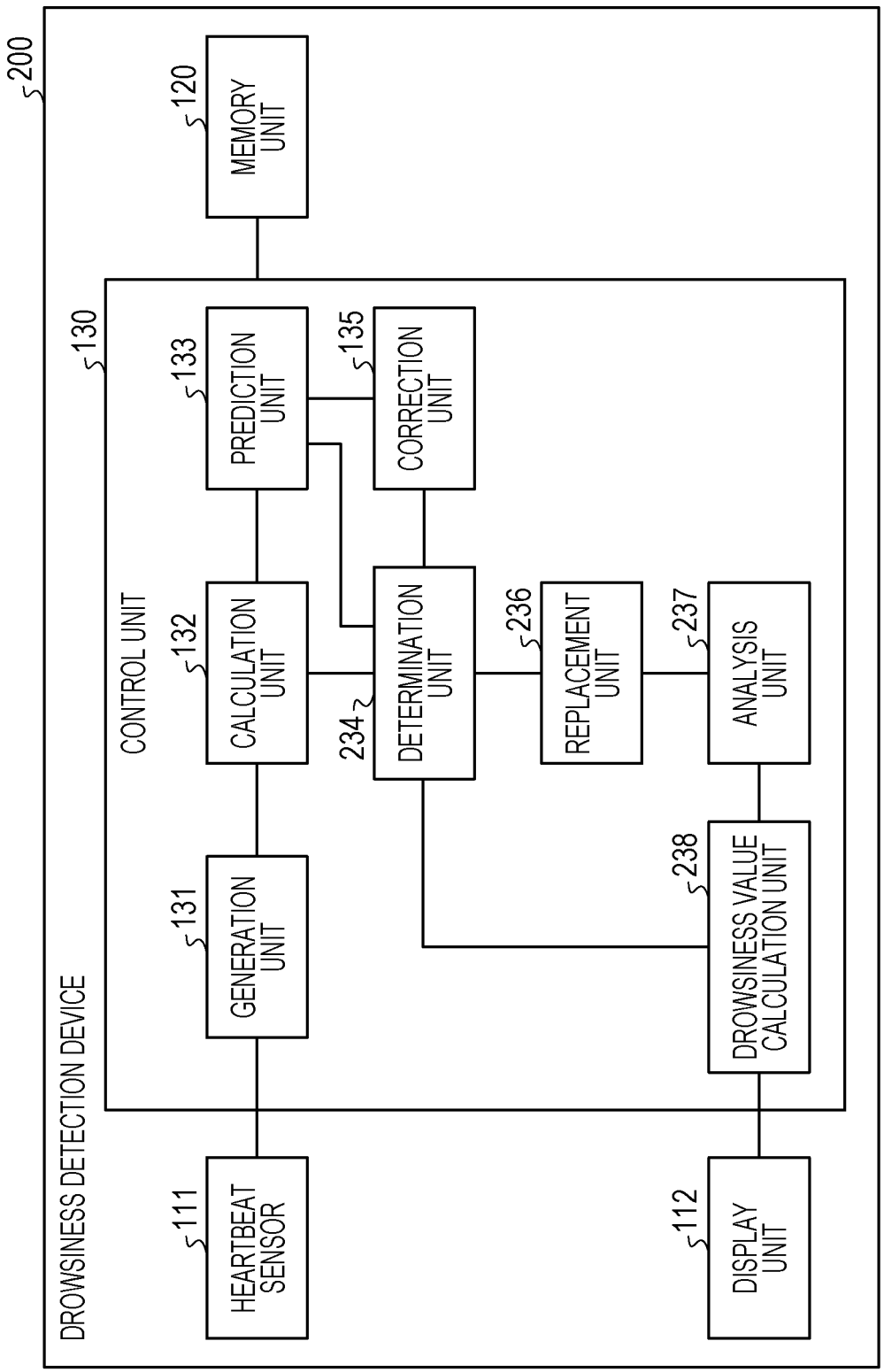
FIG. 9 is a block diagram illustrating an example of a configuration of a drowsiness detection device of a second embodiment.

In the first embodiment, mixing of the abnormal signal is determined based on the RRI data row. The mixing of the abnormal signal, however, may be determined based on the drowsiness value, and the embodiment of this case will be described as a second embodiment. FIG. 9 is a block diagram illustrating an example of a configuration of a drowsiness detection device of the second embodiment. Here, due to the same configuration as the drowsiness detection device 100 of the first embodiment is indicted with the same reference numerals, and descriptions of the overlapping configuration and operation are omitted.

A drowsiness detection device 200 of the second embodiment includes a determination unit 234, a replacement unit 236, an analysis unit 237, and a drowsiness value calculation unit 238, respectively, in place of the determination unit 134, the replacement unit 136, the analysis unit 137, and the drowsiness value calculation unit 138 of the drowsiness detection device 100 of the first embodiment.

The determination unit 234 performs the following process in addition the process performed by the determination unit 134. The determination 234 compares the drowsiness value obtained based on the respiration variation period according to the RRI data row of the actual measured value received from the drowsiness value calculation unit 238 and a predicted drowsiness value obtained based on the predicted subsequent period structure in the respiration variation model. That is, the determination unit 234 compares the drowsiness value obtained based on the RRI data row of the actual measured value and the predicted drowsiness value obtained based on the RRI data row which is replaced with the period structure of the respiration variation model. The determination unit 234 determines whether or not the abnormal signal is mixed as a result of comparison between the drowsiness value based on the actual measured value and the predicted drowsiness value. In a case where the determination unit 234 determines that the abnormal signal is mixed, the determination unit 234 outputs, to the replacement unit 236, the determination result which is based on the drowsiness value and indicates that the abnormal signal is mixed. In a case where the determination unit 234 determines that the abnormal signal is not mixed, the determination unit 234 outputs, to the replacement unit 236, the determination result which is based on the drowsiness value and indicates that the abnormal signal is not mixed.

The replacement unit 236 performs the following process in addition to the process performed by the replacement unit 136. The replacement unit 236 replaces the RRI data row of a period or periods which corresponds to the drowsiness value with the period structure of the respiration variation model according to the determination result based on the drowsiness value. When receiving the determination result from the determination unit 234 which is based on the drowsiness value and indicates that the abnormal signal is mixed, the replacement unit 236 replaces, with the period structure of the respiration variation model, the RRI data row of a period or periods corresponding to the drowsiness value in which the abnormal signal is determined to be mixed. The replacement unit 236 outputs, to the analysis unit 237, the RRI data row in the period structure of the respiration variation model, the RRI data row which is obtained by replacing an RRI data row of a period or periods corresponding to a drowsiness value determined as including an abnormal signal.

When receiving, from the determination unit 234, the determination result based on the drowsiness value in which the abnormal signal is not mixed, the replacement unit 236 does not perform replacement to the period structure of the respiration variation model.

In addition, regardless of the determination result, based on the RRI data row, of whether or not the abnormal signal is mixed, the replacement unit 236 carries out resampling on the RRI data row of one period in which a sequential update of the RRI data row is carried out. The replacement unit 236 outputs, to the analysis unit 237, the RRI data row which includes one period in which resampling is carried out, that is, the RRI data row of the actual measured value.

The analysis unit 237 receives, from the replacement unit 236, the RRI data row in the period structure of the respiration variation model, the RRI data row being obtained by replacing, and the RRI data row of the actual measured value. In the same manner as in the analysis unit 137, the analysis unit 237 performs the spectral analysis on both RRI data rows received from the replacement unit 236 to transform the both RRL data rows to respective sets of spectral density data. The analysis unit 237 outputs, to the drowsiness value calculation unit 238, the respective sets of spectral density data obtained by transformation.

When receiving the respective sets of spectral density data from the analysis unit 237, the drowsiness value calculation unit 238 calculates the drowsiness value to determine the drowsiness level based on the respective sets of spectral density data in addition of the process performed by the drowsiness value calculation unit 138. That is, the drowsiness value calculation unit 238 calculates the drowsiness value based on the RRI data row of the actual measured value and the predicted drowsiness value based on the RRI data row obtained by replacing into the period structure of the respiration variation model. The drowsiness value calculation unit 238 outputs the calculated drowsiness value and the predicted drowsiness value to the determination unit 234.

Figure 10:
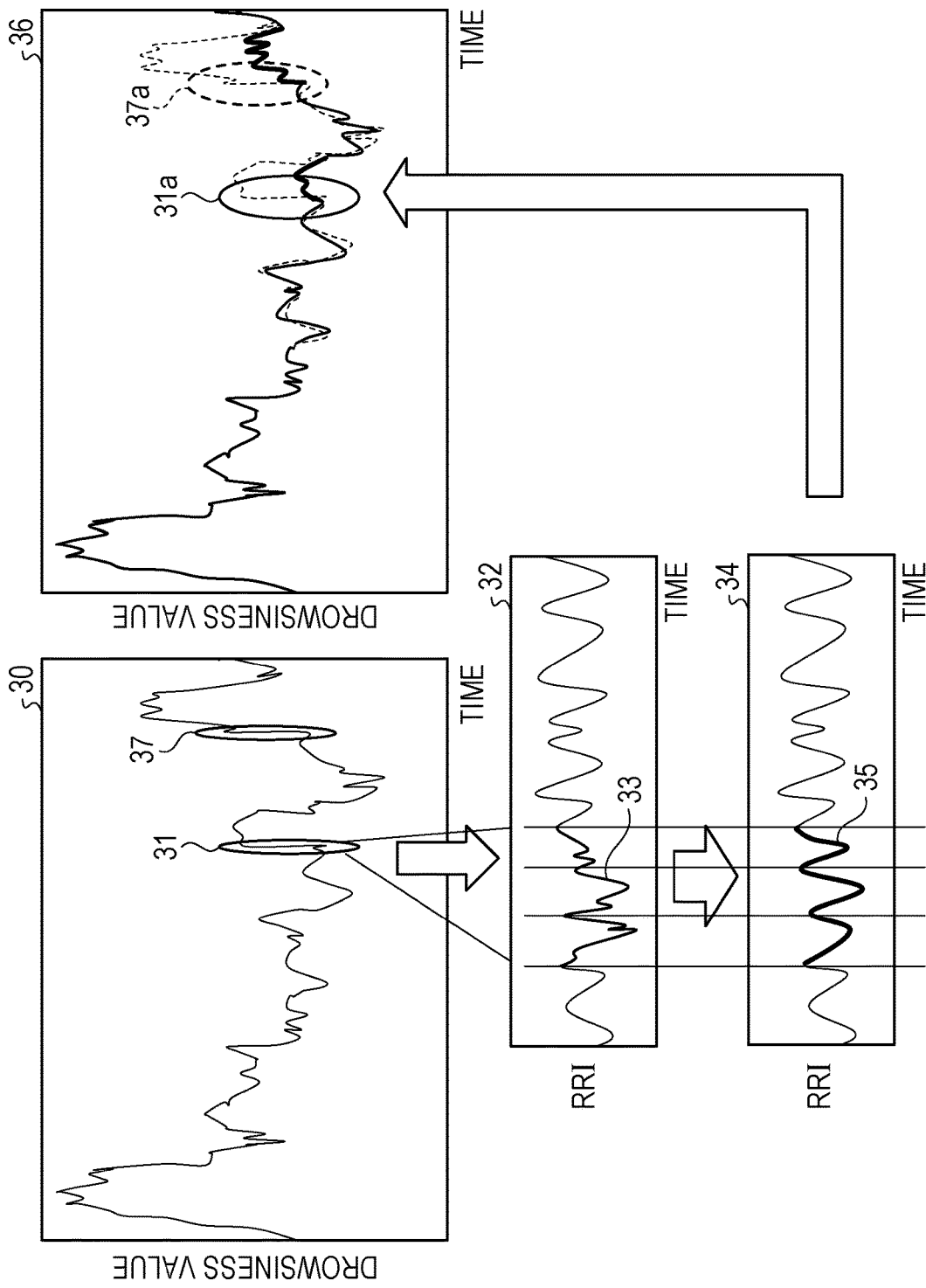
FIG. 10 is a diagram illustrating an example of determining an abnormal signal based on a drowsiness value.

Referring to FIG. 10, determination of the abnormal signal is described based on the drowsiness value. FIG. 10 is a diagram illustrating an example of determining the abnormal signal based on a drowsiness value. The graph 30 illustrated in FIG. 10 is a graph which indicates a change of the drowsiness value with time. It is assumed that the graph 30 includes regions 31 and 37 each of the drowsiness value including an abnormal signal. A graph 32 illustrates the RRI data row corresponding to the vicinity of the region 31. A waveform 33 in the graph corresponds to three periods of the respiration variation and includes noise. The waveform 33 may be determined incorrectly as including no abnormal signal by determining whether or not the abnormal signal is included based on the RRI data row. The graph 30 of the drowsiness value, however, is affected by noise. Even in such a case, the drowsiness detection device 200 of the second embodiment replaces the region 31 of the drowsiness value including the abnormal signal with the period structure of the respiration variation model, as illustrated in a waveform 35 in the graph 34. Thereby, the drowsiness detection device 200 may remove influence of noise such as illustrated in a region 31a of a graph 36. In addition, the drowsiness detection device 200 may remove influence of noise such as illustrated in a region 37a of the graph 36 in the same manner as in the region 37 of the graph 30.

Figure 11:
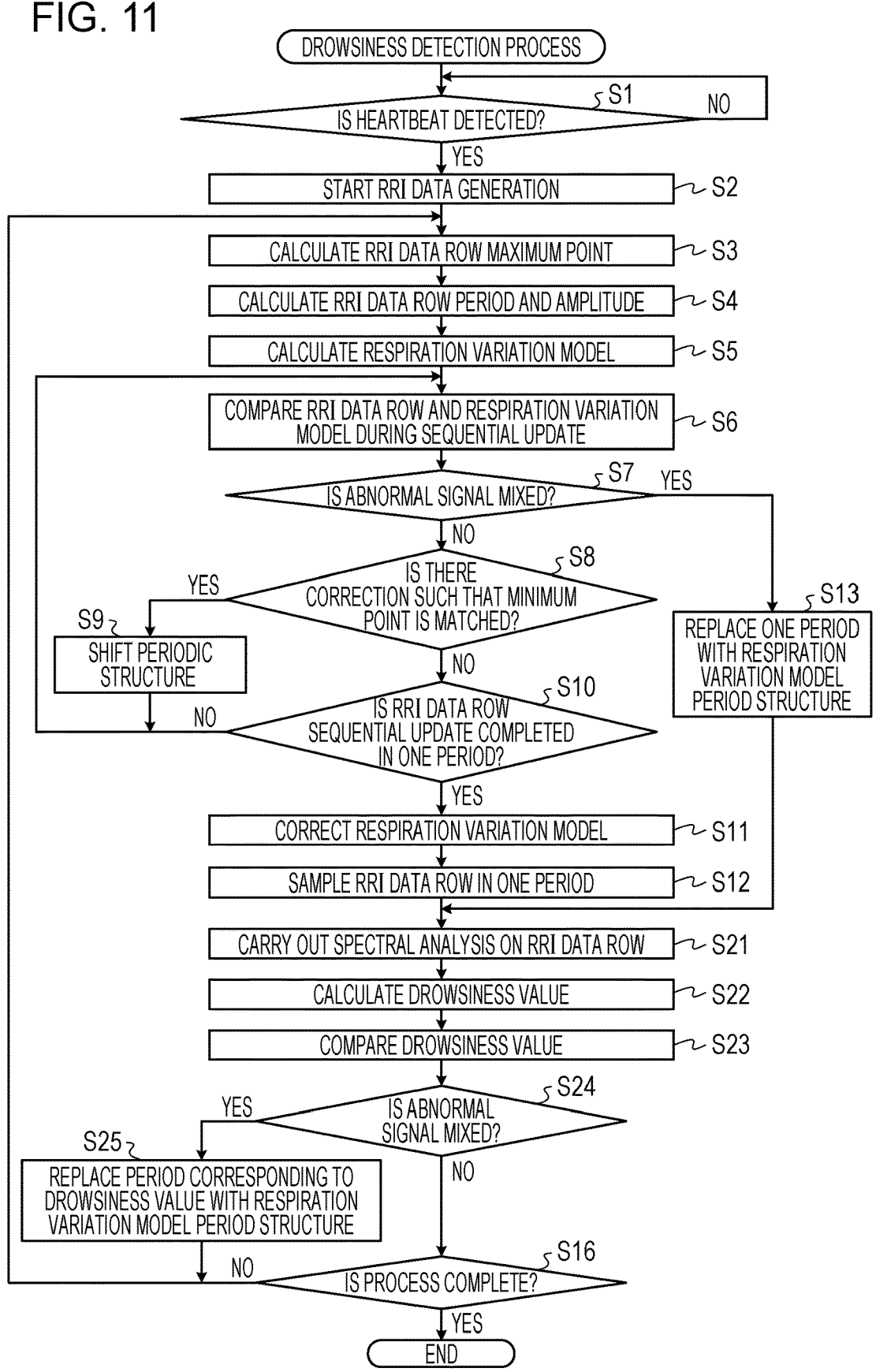
FIG. 11 is a flow chart illustrating an example of the drowsiness detection process of the second embodiment.

Next, the performance of the drowsiness detection device 200 of the second embodiment will be described. FIG. 11 is a flow chart illustrating an example of the drowsiness detection process of the second embodiment. In the description below, since the processes of steps S1 to S13 and S16 are the same as in the first embodiment, description is omitted.

The drowsiness detection device 200 executes a subsequent process continuous to the process of step S12 or S13. In the analysis unit 237, when receiving, from the replacement unit 236, the RRI data row in the period structure of the respiration variation model obtained by replacing and the RRI data row of the actual measured value, each of the RRI data rows is converted to corresponding spectral density data (step S21). The analysis unit 237 outputs, to the drowsiness value calculation unit 238, both sets of the spectral density data obtained by the conversion.

When receiving the sets of the spectral density data obtained by the conversion from the analysis unit 237, the drowsiness value calculation unit 238 calculates the drowsiness value based on each of the sets of the spectral density data. The drowsiness value calculation unit 238 calculates the drowsiness value based on the RRI data row of the actual measured value and the predicted drowsiness value based on the RRI data row, which is obtained by replacement, in the period structure of the respiration variation model (step S22). The drowsiness value calculation unit 238 outputs the calculated drowsiness value and predicted drowsiness value to the determination unit 234.

When receiving the drowsiness value and the predicted drowsiness value from the drowsiness value calculation unit 238, the determination unit 234 compares the drowsiness value and the predicted drowsiness value (step S23). The determination unit 234 determines whether or not the abnormal signal is mixed based on a result of comparison between the drowsiness value and the predicted drowsiness value (step S24). In a case where the determination unit 234 determines that the abnormal signal is not mixed (step S24: NO), the determination unit 234 outputs, to the replacement unit 236, the determination result which indicates an absence of the abnormal signal, the determination result being obtained based on the drowsiness value, and the process proceeds to the process of step S16.

In a case where the determination unit 234 determines that the abnormal signal is mixed (step S24: YES), the determination unit 134 output, to the replacement unit 236, the determination result which is obtained based on the drowsiness value and indicates that the abnormal signal is mixed. When receiving, from the determination unit 234, the determination result which is obtained based on the drowsiness value and indicates that the abnormal signal is mixed, the replacement unit 236 replaces, with the periodic structure of the respiration variation model, the RRI data row of a period or periods corresponding to the drowsiness value which leads to the determination of the presence of the mixing of the abnormal (step S25). The replacement unit 236 outputs, to the analysis unit 237, the RRI data row in the period structure of the respiration variation model, the RRI data row which is obtained by replacing an RRI data row of a period or periods corresponding to a drowsiness value determined as including an abnormal signal, and then the process rerurns to step S3. Thereby, since the drowsiness detection device 200 detects and replaces the abnormal signal which is difficult to be detected by the determination of mixing of the abnormal signal based on the RRI data row, it is possible for the drowsiness detection device 200 to secure continuity of the drowsiness estimate while improving the accuracy of the drowsiness estimate. In addition, the drowsiness detection device 200 may quickly determine a spectral abnormality.

In this manner, furthermore, the drowsiness detection device 200 calculates the drowsiness value based on the respiration variation period, and the predicted drowsiness value based on the predicted subsequent period structure. In addition, the drowsiness detection device 200 determines whether or not an abnormal signal is mixed in the heartbeat interval data by comparing the drowsiness value and the predicted drowsiness value. As a result, it is possible to secure continuity of the drowsiness estimate while improving accuracy of the drowsiness estimate.

Third Embodiment

Figure 12:
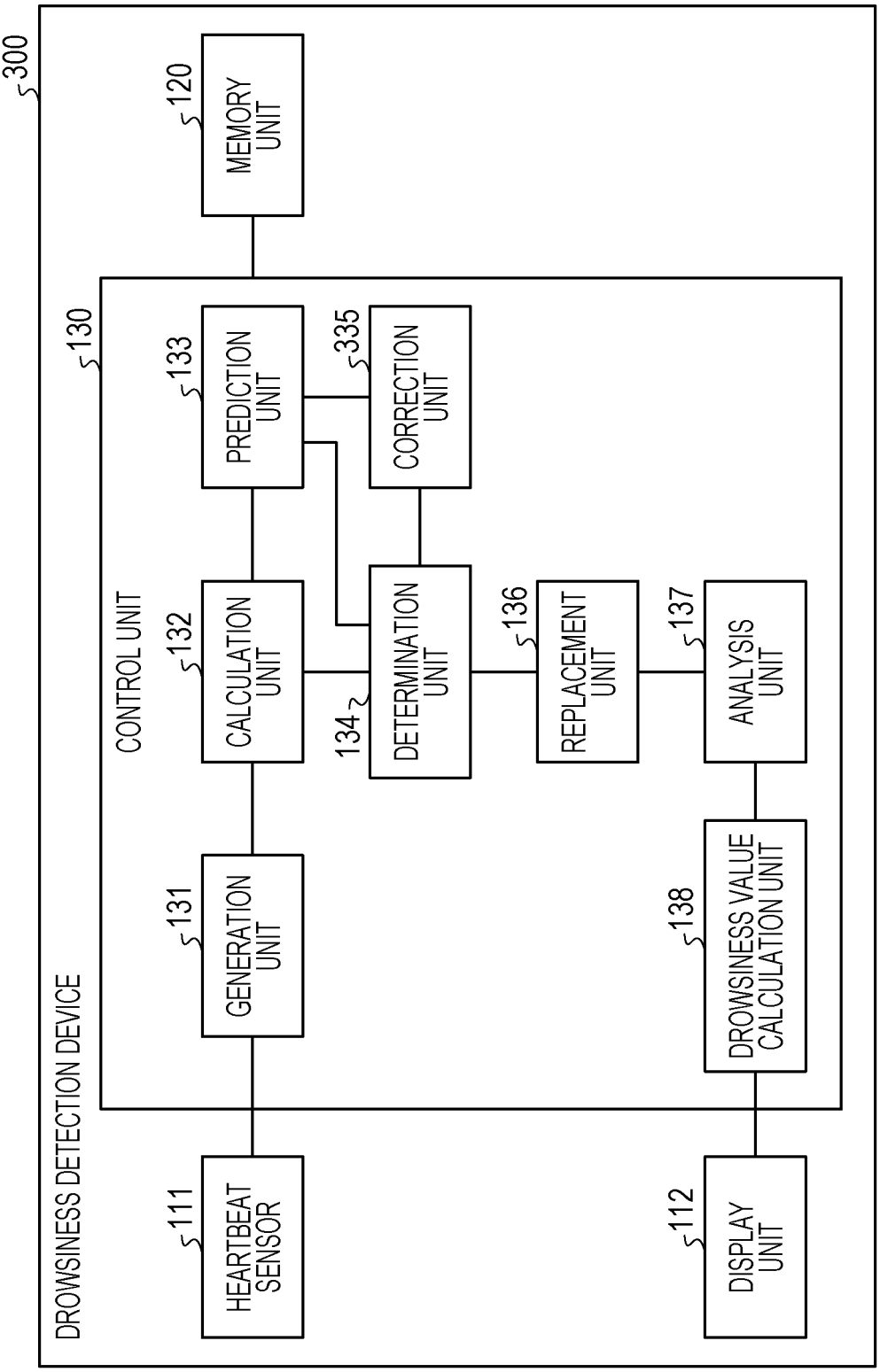
FIG. 12 is a block diagram illustrating an example of a configuration of a drowsiness detection device of a third embodiment.

In the first embodiment, in a case where the shift amount of the predicted subsequent period structure is less than a predetermined value, the local minimum points are corrected so as to match, but in a case where the shift amount is a predetermined amount or more, a further one period may be predicted and corrected, and the embodiment in this case is described as a third embodiment. FIG. 12 is a block diagram illustrating an example of a configuration of a drowsiness detection device of the third embodiment. Here, due to the same configuration as the drowsiness detection device 100 of the first embodiment being indicated with the same reference numerals, description of the overlapping configuration and of the operation are omitted.

A drowsiness detection device 300 of the third embodiment includes a correction unit 335 in place of the correction unit 135 of the drowsiness detection device 100 of the first embodiment.

The correction unit 335 performs a process described below in addition to a process same as the process carried out by the correction unit 135. When the shift amount of difference between the periodic structure of the actual measured value of the RRI data row and a first predicted periodic structure of the respiration variation model is different by 20% or more of one period of the first predicted period structure, the correction unit 335 predicts and corrects the period structure including the first predicted period structure of one period and a second predicted period structure of one period subsequent to the first predicted period structure.

The correction unit 335, in particular, shifts and corrects the first predicted period structure of the respiration variation model so as to match the local minimum point of the first predicted period structure of the respiration variation model to the local minimum point of the respiration variation period based on the RRI data row during sequential update. When performing correction in which the local minimum points is matched each other, the correction unit 335 determines whether or not the shift amount is a predetermined value or more. In a case where the shift amount is the predetermined value or more, the correction unit 335 predicts the second period structure, as a second predicted period structure, of the further one period from the local maximum point on an end point side of the first predicted period structure prior to shifting. The correction unit 335 corrects the respiration variation model which is used in prediction of the subsequent period structure based on the predicted period structure. That is, the correction unit 335 predicts the period structure of two periods of the respiration variation model. The correction unit 335 outputs the corrected respiration variation model to the prediction unit 133. Here, in a case where the shift amount is not the predetermined value or more, the correction unit 335 does not perform correction of the respiration variation model in the second period structure.

Figure 13:
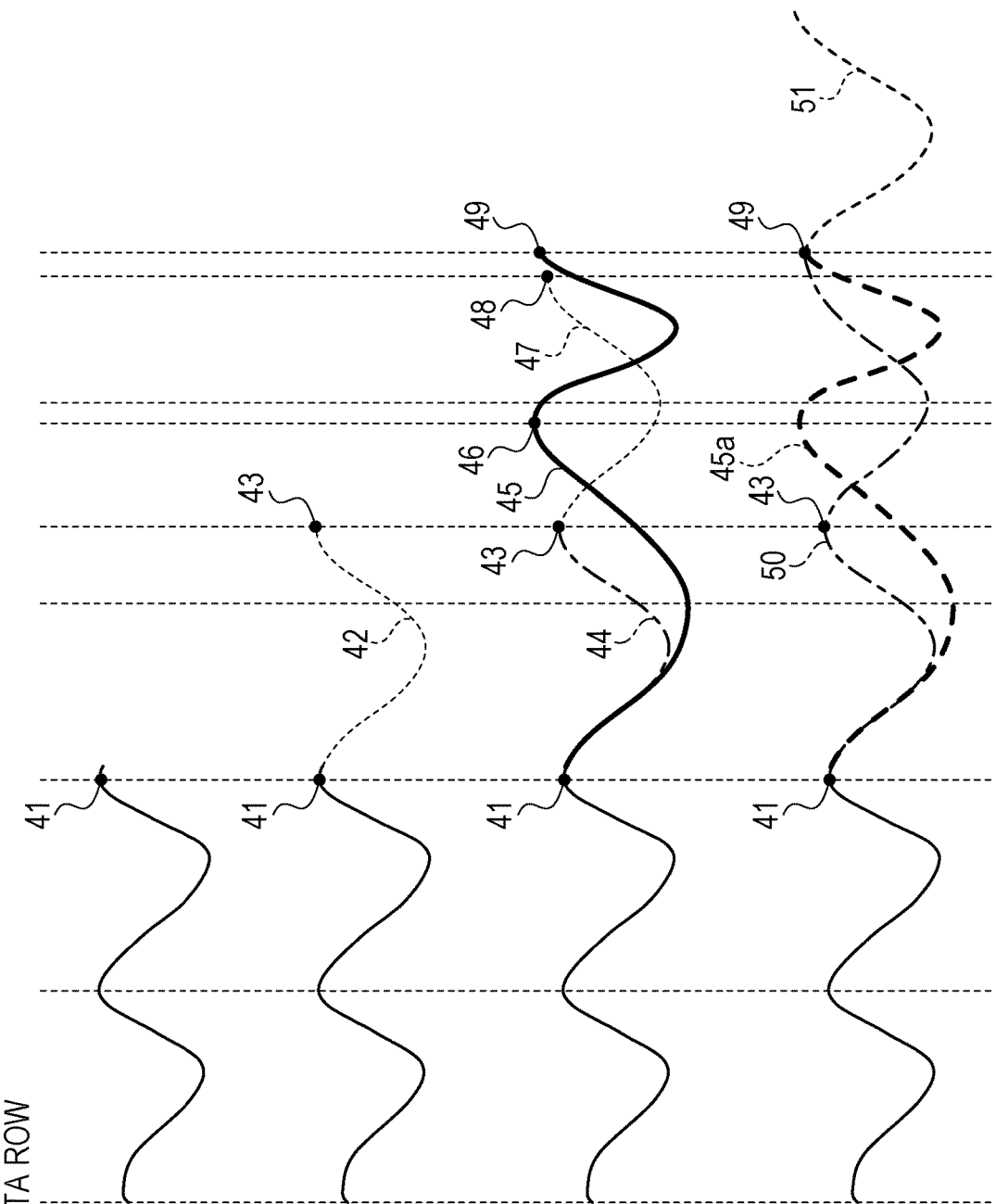
FIG. 13 is a diagram illustrating an example of conversion in a case where a shifted period structure is shifted by a predetermined value or more.

Here, referring to FIG. 13, there is described correction of the respiration variation model of a case where the shifted period structure is shifted by the predetermined value or more. FIG. 13 is a diagram illustrating an example of replacement in a case where a shifted period structure is shifted by a predetermined value or more. As illustrated in FIG. 13, in the respiration variation model, a period structure 42 is predicted from a point as a local maximum point 41 of the RRI data row, and the subsequent local maximum point 43 is predicted. In the example in FIG. 13, it is assumed that a local maximum point 46 of the actual measured value is shifted 20% or more of one period of a predicted and confirmed period structure 44 from the local maximum point 43 of the predicted period structure 44 when a period structure 45 of the RRI data row of the actual measured value is sequentially updated. For this reason, the correction unit 335 predicts a period structure 47 of the further one period from the local maximum point 43. After that, when the period structure 45 of the RRI data row of the actual measured value is updated from the local maximum point 41 to a local maximum point 49 apart from the local maximum point 41 by two period, the correction unit 335 shifts the local maximum point 48 of the period structure 47 so as to match the local maximum point 49. That is, the correction unit 335 replaces, with a period structure 50, the period structure 45 of the RRI data row of the actual measured value of two periods from the local maximum point 41 to the local maximum point 49. That is, in the example of FIG. 13, a period structure 45a having a distorted waveform of two periods is replaced with a period structure 50 of two periods. In addition, in the prediction unit 133, a subsequent period structure 51 is predicted based on the respiration variation model calculated by the correction unit 335, that is, the respiration variation model corrected by the period structure 50.

Figure 14:
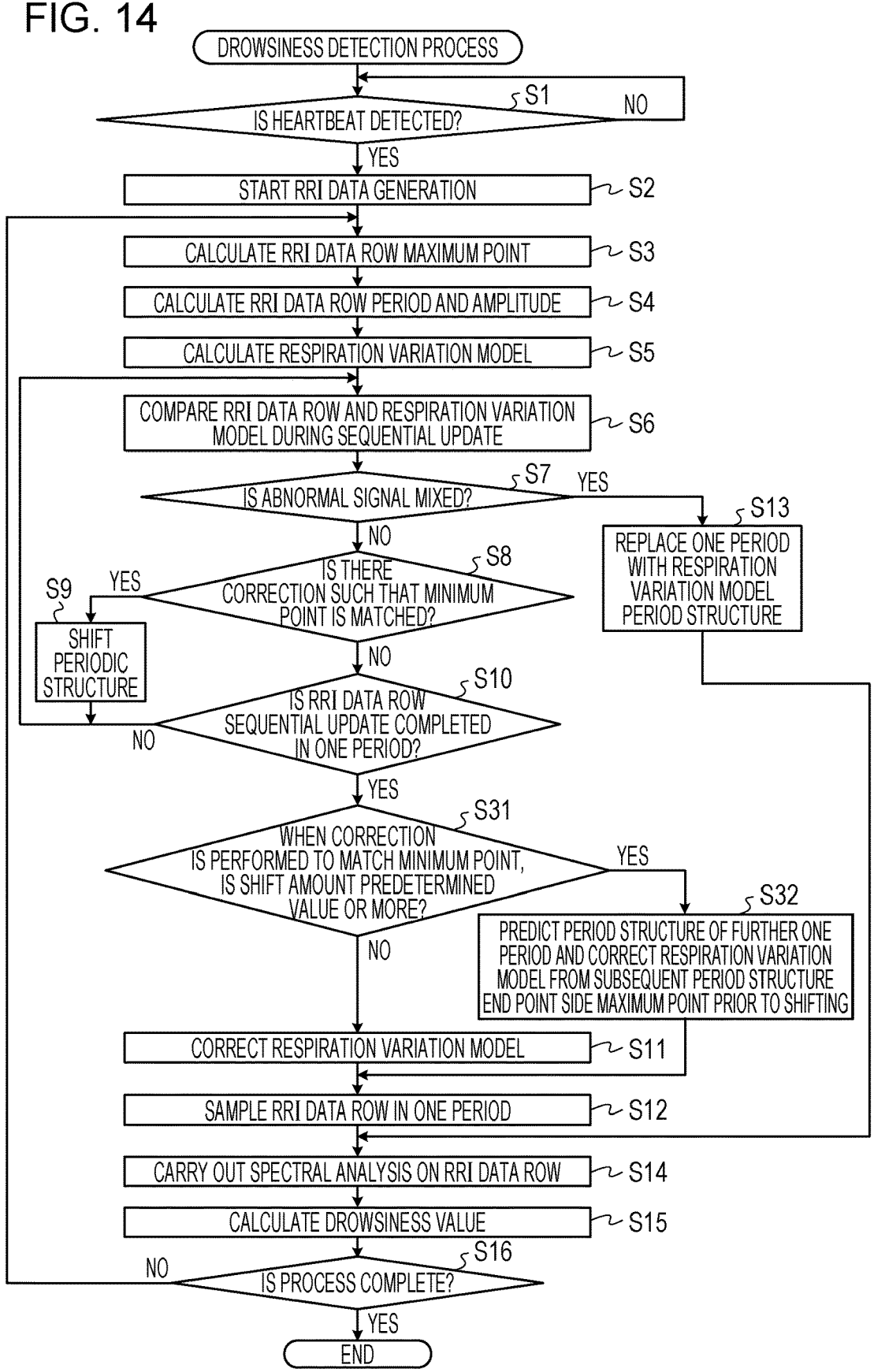
FIG. 14 is a flow chart illustrating an example of the drowsiness detection process of the third embodiment.

Next, the configuration of the drowsiness detection device 300 of the third embodiment will be described. FIG. 14 is a flow chart illustrating an example of the drowsiness detection process of the third embodiment. In the description below, since processes of steps S1 to S16 are the same as in the first embodiment, the description is omitted.

The drowsiness detection device 300 executes a subsequent process continuous to the process of step S10. When performing correction in which the local minimum points are matched, the correction unit 335 determines whether or not the shift amount is a predetermined value or more (step S31). In a case where the shift amount is the predetermined value or more (step S31: YES), the correction unit 335 predicts the period structure of the further one period from the local maximum point on the end point side in the subsequent period structure prior to shifting and corrects the respiration variation model (step S32). In the correction unit 335, in a case where the shift amount is not the predetermined value or more (step S31: NO), the process proceeds to step S11. Thereby, since the drowsiness detection device 300 replaces the period structure in which noise is mixed in a case where a great amount of noise is mixed, it is possible to secure continuity of the drowsiness estimate while improving the accuracy of the drowsiness estimate. That is, the drowsiness detection device 300 is able to achieve stability of estimation precision using a low-order AR model. In addition, the drowsiness detection device 300 is able to mitigate deterioration of precision of spectral calculation using a low-order model by following only the period component of a predetermined region (for example, from a reference to +20%).

In this manner, in a case where the shifted subsequent period structure is shifted from the subsequent period structure prior to shifting by the predetermined value or more, the drowsiness detection device 300 predicts the period structure of the further one period from the local maximum point on an end point side in the subsequent period structure prior to shifting. In addition, the drowsiness detection device 300 corrects the respiration variation model which is used in prediction of the subsequent period structure based on the predicted period structure. As a result, it is possible to secure continuity of the drowsiness estimate while improving accuracy of the drowsiness estimate.

Fourth Embodiment

Figure 15:
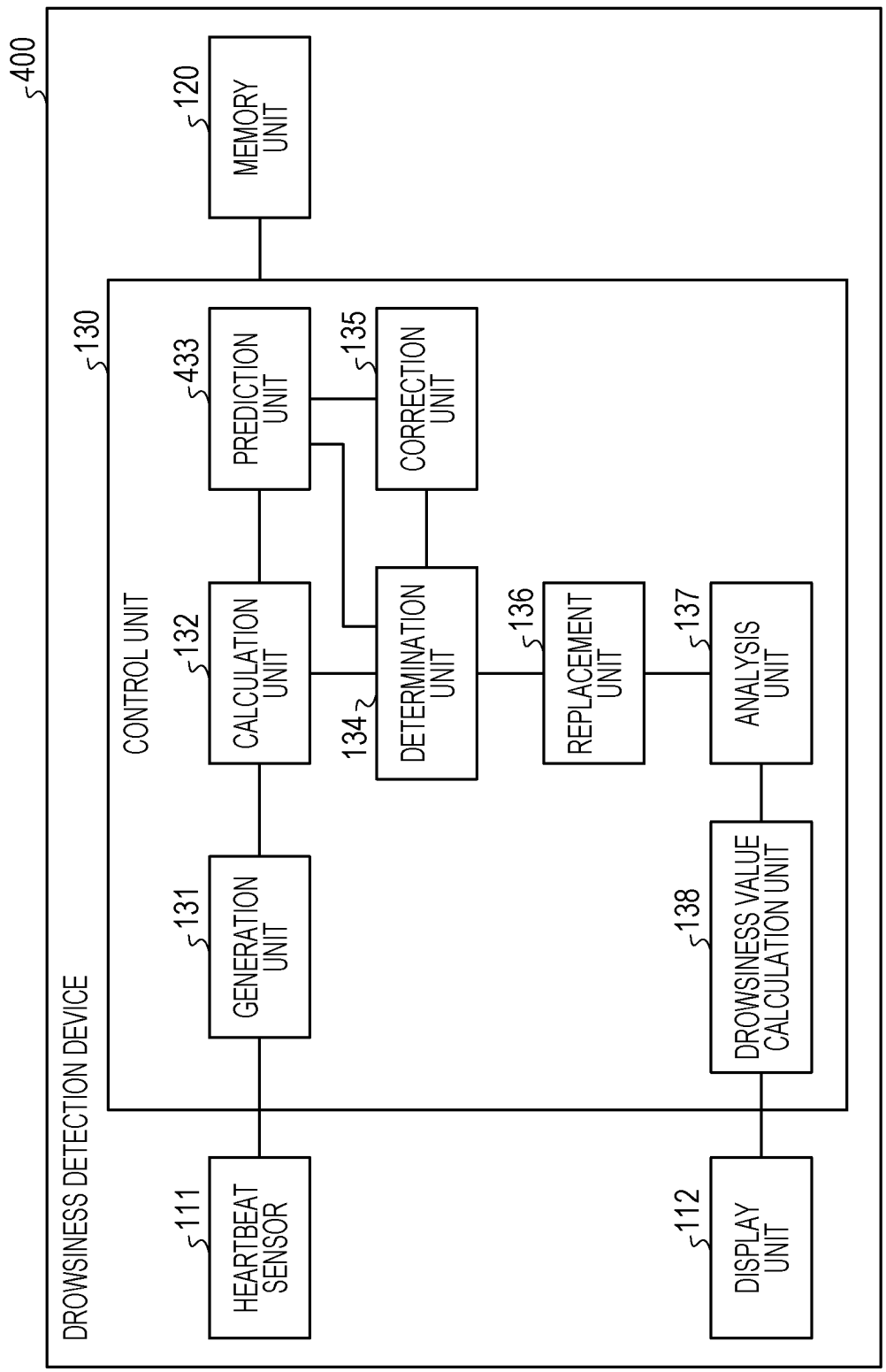
FIG. 15 is a block diagram illustrating an example of a configuration of a drowsiness detection device of a fourth embodiment.

In the first embodiment, the respiration variation model is predicted based on the period and amplitude of the RRI data row. The respiration variation model may, however, be predicted considering the component at the low frequency side (LF) of the respiration variation period, and the embodiment of this case will be described as a fourth embodiment. FIG. 15 is a block diagram illustrating an example of a configuration of a drowsiness detection device of the fourth embodiment. Here, due to the same configuration as the drowsiness detection device 100 of the first embodiment being indicted with the same reference numerals, descriptions of the overlapping configuration and the operation are omitted.

A drowsiness detection device 400 of the fourth embodiment includes a prediction unit 433 in place of the prediction unit 133 of the drowsiness detection device 100 of the first embodiment.

The prediction unit 433 predicts the subsequent period structure of the respiration variation considering variation of a long period in addition to the process in the prediction unit 133. The prediction unit 433 calculates the local maximum point trend which indicates change of the local maximum point, the local minimum point trend which indicates change of the local minimum point, and the amplitude trend which indicates change of the amplitude based on the periods of past respiration variation within an integrated interval of the RRI data row and the period of the input respiration variation. The prediction unit 433 calculates the respiration variation model to predict the subsequent period structure based on the past respiration variation periods within an integrated interval of the RRI data row, the input respiration variation period, the calculated local maximum point trend, the local minimum point trend, and the amplitude trend. The prediction unit 433 outputs the respiration variation model which includes the predicted subsequent period structure to the determination unit 134 and the correction unit 135.

Figure 16:
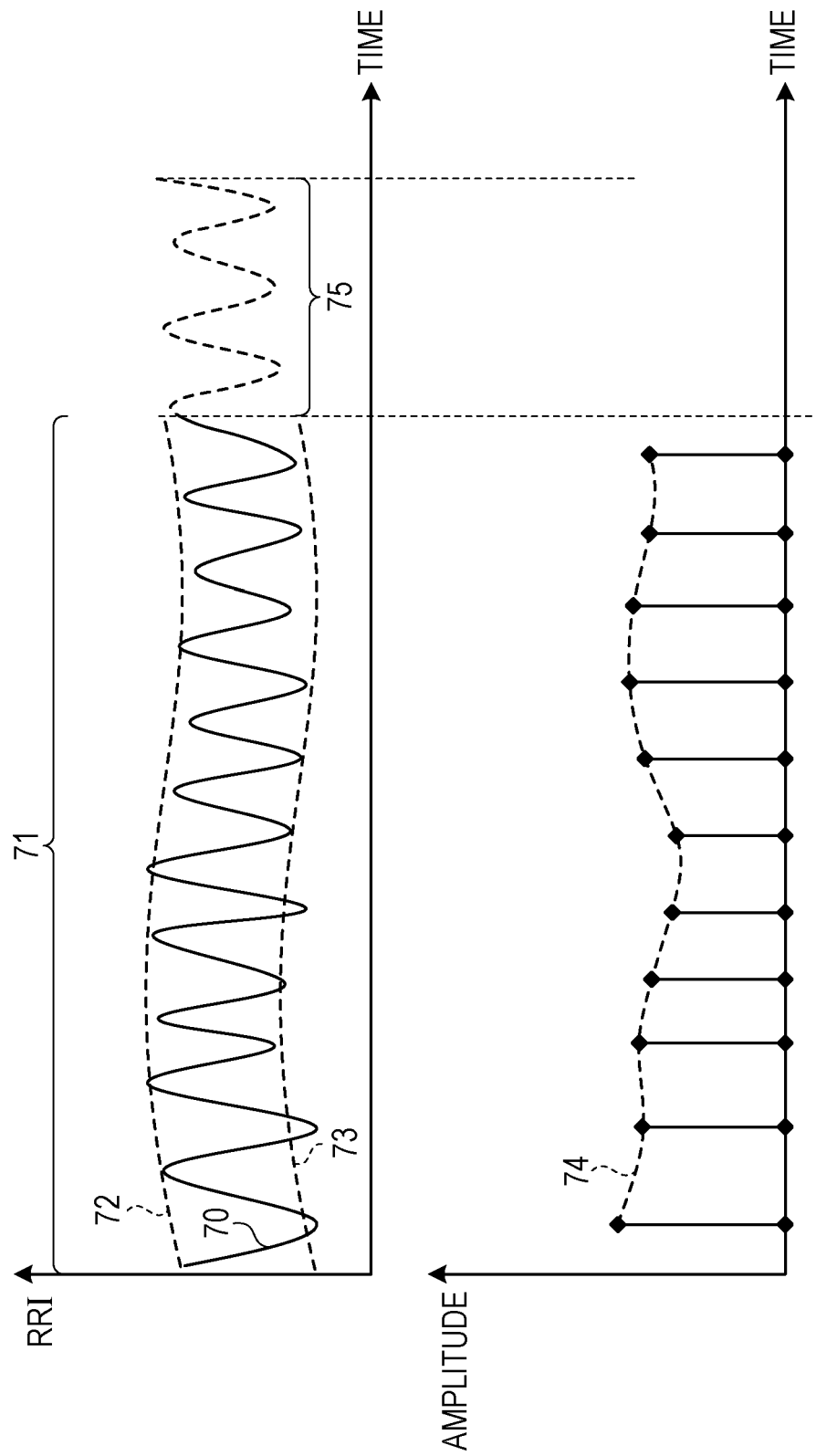
FIG. 16 is a diagram illustrating an example of prediction which reflects a long period trend.

There will be described prediction of the subsequent period structure based on each trend using FIG. 16. FIG. 16 is a diagram illustrating an example of prediction which reflects a long period trend. As illustrated in FIG. 16, in the respiration variation graph 70 which is the RRI data row, the prediction unit 433 calculates a local maximum point trend 72, a local minimum point trend 73, and an amplitude trend 74 from the respiration variation periods in the determined interval 71. The prediction unit 433 calculates, based on the respiration variation period, the calculated local maximum point trend 72, the local minimum point trend 73, and the amplitude trend 74, the respiration variation model to predict the period structure in a future interval 75. Here, in the example of FIG. 16, the respiration variation model is calculated based on each trend, and each trend is reflected in the prediction of the period structure of three periods.

Figure 17:
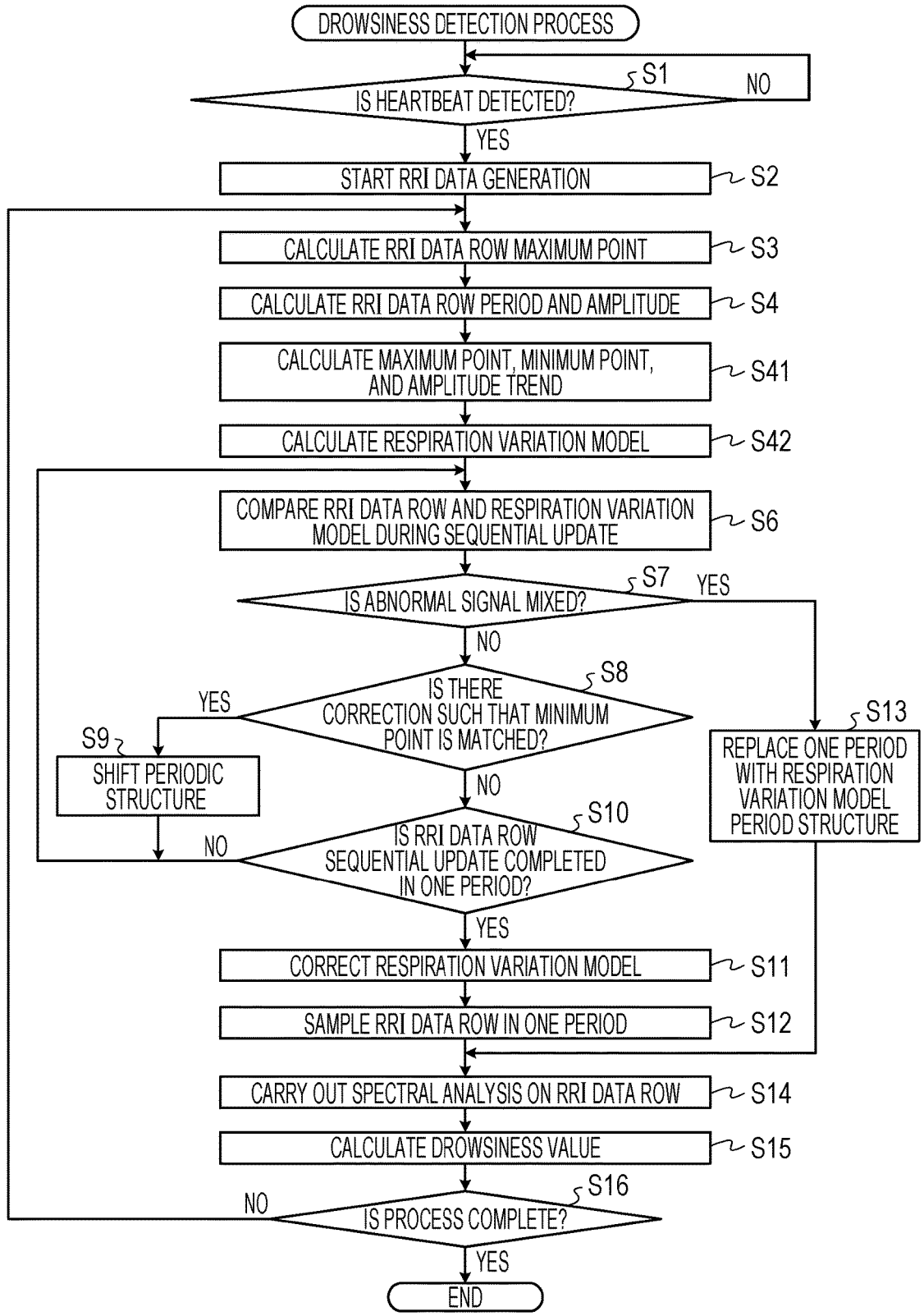
FIG. 17 is a flow chart illustrating an example of the drowsiness detection process of the fourth embodiment.

Next, the configuration of the drowsiness detection device 400 of the fourth embodiment will be described. FIG. 17 is a flow chart illustrating an example of the drowsiness detection process of the fourth embodiment. In the description below, since processes of steps S1 to S4, and S6 to S16 are the same as in the first embodiment, the descriptions are omitted.

The drowsiness detection device 400 executes subsequent processes continuous to the process of step S4 and the subsequent processes will be explained. When receiving the respiration variation period and the RRI data row from the calculation unit 132, the prediction unit 433 calculates, based on the respiration variation period, trends of the local maximum point, the local minimum point, and the amplitude (step S41). The prediction unit 433 calculates the respiration variation model to predict the subsequent period structure based on the respiration variation period and the calculated trends of the calculated local maximum point, the local minimum point, and the amplitude (step S42). The prediction unit 433 outputs, to the determination unit 134 and the correction unit 135, the respiration variation model which includes the predicted subsequent period structure, and the process proceeds to step S6. Thereby, since the drowsiness detection device 400 considers a component of the long period which is equivalent to blood pressure variation, even when there is noise for a long period, it is possible to secure continuity of the drowsiness estimate while checking deterioration of accuracy of the drowsiness estimate.

In this manner, the drowsiness detection device 400 calculates, based on the calculated respiration variation period, the local maximum point trend which indicates change of the local maximum point, the local minimum point trend which indicates change of the local minimum point, and the amplitude trend which indicates change of the amplitude. In addition, the drowsiness detection device 400 predicts the subsequent period structure of the respiration variation based on the calculated local maximum point trend, the local minimum point trend, and the amplitude trend. Accordingly, it is possible to secure continuity of the drowsiness estimate while preventing deterioration of accuracy of the drowsiness estimate.

In addition, each configuration element of each unit which is illustrated may be configured physically other than as illustrated. That is, the specific mode of distributed form or integrated form of each unit is not limited to the illustration.

It is possible to configure functionally or physically the entirety or a portion of each unit in a distributed or integrated form according to various loads, usage conditions, and the like. For example, the generation unit 131 and the calculation unit 132 may be integrated. In addition, each process which is illustrated does not have to be limited to the above order, and in a range that does not contradict the processing contents, may be simultaneously implemented, and may be implemented in a switched order.

Furthermore, various process functions which are performed by each device may be executed by the entirety or an arbitrary portion on the CPU (or a micro computer such as the MPU or a micro controller unit (MCU)) as an example of processor that performs various control and arithmetic operations. In addition, the entirety or an arbitrary portion of various process functions may be executed on a program which is executed using the CPU (or a micro computer such as the MPU or the MCU), or on hardware using wired logic.

Here, various processes which are described in each of the embodiments above are able to be realized by executing a program prepared in advance using a computer as an example of processor that performs various control and arithmetic operations. Therefore, an example of the computer which executes the program that has the same function as the embodiments above will be described below. FIG. 18 is a diagram illustrating an example of a computer which executes a drowsiness detection program.

As illustrated in FIG. 18, a computer 500 includes a CPU 501, as an example of processor, which executes various arithmetic processes, an input device 502 which receives data input, and a monitor 503. In addition, the computer 500 includes a medium reading device 504 which reads a program or the like from a storage medium such as a non-transitory computer-readable recording medium, an interface device 505 for connecting various devices, and a communication device 506 for connecting wiredly or wirelessly to other information processing devices and the like. In addition, the computer 500 includes a RAM 507 which temporarily stores various information, and a hard disk device 508. In addition, each device 501 to 508 is coupled to a bus 509.

A drowsiness detection program which functions in the same manner as each processing unit of the generation unit 131, the calculation unit 132, the prediction unit 133, the determination unit 134, the correction unit 135, the replacement unit 136, the analysis unit 137, and the drowsiness value calculation unit 138 which are illustrated in FIG. 1 is stored on the hard disk device 508. In addition, a drowsiness detection program which functions in the same manner as each processing unit of the generation unit 131, the calculation unit 132, the prediction unit 133, the determination unit 234, the correction unit 135, the replacement unit 236, the analysis unit 237, and the drowsiness value calculation unit 238 which are illustrated in FIG. 9 may be stored on the hard disk device 508. In addition, a drowsiness detection program which functions in the same manner as each processing unit of the generation unit 131, the calculation unit 132, the prediction unit 133, the determination unit 134, the correction unit 335, the replacement unit 136, the analysis unit 137, and the drowsiness value calculation unit 138 which are illustrated in FIG. 12 may be stored on the hard disk device 508. In addition, a drowsiness detection program which functions in the same manner as each processing unit of the generation unit 131, the calculation unit 132, the prediction unit 433, the determination unit 134, the correction unit 135, the replacement unit 136, the analysis unit 137, and the drowsiness value calculation unit 138 which are illustrated in FIG. 15 may be stored on the hard disk device 508. In addition, various data is stored on the hard disk device 508 in order to realize the drowsiness detection program such as the respiration variation model.

For example, an input device 502 receives input of various information such as operation information and management information from the subject or an operator who is a user of a computer 500. For example, a monitor 503 displays various screens such as a warning screen for the user or the manager of the computer 500. For example, the interface device 505 is coupled by a control device or the like of a vehicle. For example, a communication device 506 is coupled to a network which is not illustrated in the drawings, and exchanges with various devices and various information.

The CPU 501 performs various processes by reading each program which is stored on the hard disk device 508, and executing expansion in the RAM 507. In addition, the programs are able to cause the computer 500 to function as the generation unit 131, the calculation unit 132, the prediction unit 133, the determination unit 134, the correction unit 135, the replacement unit 136, the analysis unit 137, and the drowsiness value calculation unit 138 which are illustrated in FIG. 1. In addition, the programs may cause the computer 500 to function as the generation unit 131, the calculation unit 132, the prediction unit 133, the determination unit 234, the correction unit 135, the replacement unit 236, the analysis unit 237, and the drowsiness value calculation unit 238 which are illustrated in FIG. 9. In addition, the programs may cause the computer 500 to function as the generation unit 131, the calculation unit 132, the prediction unit 133, the determination unit 134, the correction unit 335, the replacement unit 136, the analysis unit 137, and the drowsiness value calculation unit 138 which are illustrated in FIG. 12. In addition, the programs may cause the computer 500 to function as the generation unit 131, the calculation unit 132, the prediction unit 433, the determination unit 134, the correction unit 135, the replacement unit 136, the analysis unit 137, and the drowsiness value calculation unit 138 which are illustrated in FIG. 15.

Here, the drowsiness detection program does not have to be stored on the hard disk device 508. For example, the program which is stored on a recording medium so as to be readable by the computer 500 may be executed by reading by the computer 500. For example, the recording medium which is readable by the computer 500 corresponds to a portable storage medium such as a CD-ROM, a DVD disc, a universal serial bus (USB) memory and the like, a semiconductor memory such as a flash memory, a hard disk drive, and the like. In addition, the drowsiness detection program may be stored in a device which is coupled to a public network, the Internet, LAN, or the like, and from these the computer 500 may execute by reading the drowsiness detection program.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A drowsiness detection device comprising:
a memory; and
a processor coupled to the memory and the processor is configured to:
calculate a respiration variation period based on heartbeat interval data which is generated based on data that is obtained from a heartbeat sensor;
predict a subsequent period structure of the respiration variation period based on the calculated respiration variation period;
determine whether or not an abnormal signal is included in the heartbeat interval data by comparing the heartbeat interval data during a first sequential update and the predicted subsequent period structure; and
replace the respiration variation period which corresponds to the heartbeat interval data that includes the abnormal signal, with the predicted subsequent period structure in a case where it is determined that the abnormal signal is included.

2. The drowsiness detection device according to claim 1, wherein
the processor is further configured to:
in a case where it is determined that the abnormal signal is not included in the heartbeat interval data, shift the predicted subsequent period structure of the respiration variation period such that a local minimum point or a local maximum point of the shifted predicted subsequent period structure matches the local minimum point or the local maximum point of the respiration variation period based on the heartbeat interval data during the first sequential update; and
determine whether or not an abnormal signal is included in the heartbeat interval data by comparing the heartbeat interval data during a second sequential update and the shifted predicted subsequent period structure.

3. A drowsiness detection method comprising:
calculating, by a processor, a respiration variation period based on heartbeat interval data which is generated based on data that is obtained from a heartbeat sensor;
predicting a subsequent period structure of the respiration variation period based on the calculated respiration variation period;
determining whether or not an abnormal signal is included in the heartbeat interval data by comparing the heartbeat interval data during a first sequential update and the predicted subsequent period structure; and
replacing the respiration variation period which corresponds to the heartbeat interval data that includes the abnormal signal, with the predicted subsequent period structure in a case where it is determined that the abnormal signal is included.

4. The drowsiness detection method according to claim 3, further comprising:
in a case where it is determined that the abnormal signal is not included in the heartbeat interval data, shifting the predicted subsequent period structure such that a local minimum point or a local maximum point of the shifted predicted subsequent period structure matches the local minimum point or the local maximum point of the respiration variation period based on the heartbeat interval data during the first sequential update; and
determining whether or not an abnormal signal is included in the heartbeat interval data by comparing the heartbeat interval data during a second sequential update and the shifted predicted subsequent period structure.

5. A non-transitory computer-readable recording medium having stored therein a program that causes a computer to execute a process, the process comprising:

calculating a respiration variation period based on heartbeat interval data which is generated based on data that is obtained from a heartbeat sensor;

predicting a subsequent period structure of the respiration variation period based on the calculated respiration variation period;

determining whether or not an abnormal signal is included in the heartbeat interval data by comparing the heartbeat interval data during a first sequential update and the predicted subsequent period structure; and replacing the respiration variation period which corresponds to the heartbeat interval data that includes the abnormal signal, with the predicted subsequent period structure in a case where it is determined that the abnormal signal is included.

6. The non-transitory computer-readable recording medium according to claim 5, the process further comprising:

in a case where it is determined that the abnormal signal is not included in the heartbeat interval data, shifting the predicted subsequent period structure such that a local minimum point or a local maximum point of the shifted predicted subsequent period structure matches the local minimum point or the local maximum point of the respiration variation period based on the heartbeat interval data during the sequential update, and determining whether or not an abnormal signal is included in the heartbeat interval data by comparing the heartbeat interval data during a second sequential update and the shifted predicted subsequent period structure.

* * * * *